US009617306B2

(12) United States Patent
Rimer et al.

(10) Patent No.: US 9,617,306 B2
(45) Date of Patent: Apr. 11, 2017

(54) PEPTIDE INHIBITORS OF CALCIUM OXALATE MONOHYDRATE CRYSTALLIZATION AND USES THEREOF

(71) Applicants: Jeffrey D. Rimer, Houston, TX (US); Pankaj Karande, Troy, NY (US)

(72) Inventors: Jeffrey D. Rimer, Houston, TX (US); Pankaj Karande, Troy, NY (US)

(73) Assignees: UNIVERSITY OF HOUSTON, Houston, TX (US); RENSSELAER POLYTECHNIC INSTITUTE, Troy, NY (US)

( * ) Notice: Subject to any disclaimer, the term of this patent is extended or adjusted under 35 U.S.C. 154(b) by 0 days.

(21) Appl. No.: 14/326,908

(22) Filed: Jul. 9, 2014

(65) Prior Publication Data

US 2015/0099704 A1 Apr. 9, 2015

Related U.S. Application Data

(60) Provisional application No. 61/844,143, filed on Jul. 9, 2013.

(51) Int. Cl.
*A61K 38/10* (2006.01)
*C07K 7/08* (2006.01)
*A61P 13/00* (2006.01)
*G01N 33/53* (2006.01)
*G01N 33/68* (2006.01)
*A61K 38/00* (2006.01)

(52) U.S. Cl.
CPC .............. *C07K 7/08* (2013.01); *G01N 33/53* (2013.01); *G01N 33/6893* (2013.01); *A61K 38/00* (2013.01); *G01N 2500/04* (2013.01); *G01N 2500/20* (2013.01); *G01N 2800/345* (2013.01)

(58) Field of Classification Search
CPC .......... C07K 7/08; A61K 38/00; G01N 33/53; G01N 2500/04; G01N 2500/20; G01N 33/6893; G01N 2800/345
See application file for complete search history.

(56) References Cited

U.S. PATENT DOCUMENTS 5,279,827 A   1/1994  Costello
2009/0136594 A1   5/2009  McLeroy et al.

FOREIGN PATENT DOCUMENTS

WO   WO 2013/024048 A1 * 2/2013 ....... A61K 47/48215

OTHER PUBLICATIONS

Shiraga, Proc Natl Acad Sci USA (Jan. 1, 1992) 89(1): 426-430.*
Farmanesh (Journal of Crystal Growth (available online Sep. 23, 2012) 373: 13-19).*
Barnes (Bioinformatics for Geneticists (2003) John Wiley & Sons, Chapter 14. Amino acid Properties and Consequences of Substitutions).*
Farmanesh, et al, High-throughput Platform for Design and Screening of Peptides as Inhibitors of Calcium Oxalate Monohydrate Crystallization; Journal of Growth; Jun. 15, 2013, vol. 373, pp. 13-19.
Lieske, of al; Adhesion, Internalization and Metabolism of Calcium Oxalate Monohydrate Crystals by Renal Epithelial Cells; Kindney Int, Nov. 1997, vol. 52, No. 5, pp. 1291-1301.
Shiraga, et al; Inhibition of Calcium Oxalate Crystal Growth In Vitro by Uropontin: Another Member of the Aspartic Acid-Rich Protein Superfamily; Proc Natl Acad Sci USA, Jan. 1, 1992, vol. 89, No. 1, pp. 426-430.
George, A. and A. Veis, *Phosphorylated Proteins and Control over Apatite Nucleation, Crystal Growth, and Inhibition*. Chemical Reviews, 2008. 108(11): p. 4670-4693.
Weiner, S. and L. Addadi, *Crystallization Pathways in Biomineralization*, in Annual Review of Materials Research, vol. 41, D.R. Clarke and P. Fratzl, Editors. 2011. p. 21-40.
Stamatelou, K.K., M.E. Francis, C.A. Jones, L.M. Nyberg, and G.C. Curhan, *Time trends in reported prevalence of kidney stones in the United States*: 1976-1994. Kidney International, 2003. 63(5): p. 1817-1823.
Brikowski, T.H., Y. Lotan, and M.S. Pearle, *Climate-related increase in the prevalence of urolithiasis in the United States*. Proc Natl Acad Sci U S A, 2008. 105(28): p. 9841-6.
Coe, F.L., J.H. Parks, and J.R. Asplin, *Medical process—the pathogenesis and treatment of kidney-stones*. New England Journal of Medicine, 1992. 327(16): p. 1141-1152.
Sizemore, J.P. and M.F. Doherty, *A New Model for the Effect of Molecular Imposters on the Shape of Faceted Molecular Crystals*. Crystal Growth & Design, 2009. 9(6): p. 2637-2645.
Weissbuch, I., L. Addadi, M. Lahav, and L. Leiserowitz, *Molecular Recognition at Crystal Interfaces*. Science, 1991. 253(5020): p. 637-645.

(Continued)

*Primary Examiner* — Julie Ha
*Assistant Examiner* — Li Ni Komatsu
(74) *Attorney, Agent, or Firm* — Winstead PC

(57) ABSTRACT

In an embodiment, the present disclosure pertains to a composition for inhibiting calcium oxalate monohydrate crystal growth comprising at least one isolated polypeptide comprising a plurality of amino acids that bind the surface of the calcium oxalate monohydrate crystal; and a plurality of amino acids spacers, wherein the amino acid spacers are arranged in varying sequences between the plurality of amino acids that bind the surface of the calcium oxalate monohydrate crystal. In some embodiments, the present disclosure related to a method of controlling calcium oxalate monohydrate crystal growth in a subject in need thereof comprising administering to the subject therapeutically effective amount of the calcium oxalate monohydrate inhibiting polypeptide. In some embodiments, the present disclosure relates to a method of identifying calcium oxalate monohydrate inhibiting peptides. Such a method may comprise designing a peptide library of potential calcium oxalate inhibiting peptides; screening the peptide library for high efficacy inhibitor peptides for inhibition of calcium oxalate monohydrate crystallization; and conducting molecular characterization of the high efficacy inhibitor to determine specificity.

5 Claims, 8 Drawing Sheets

(56) References Cited

OTHER PUBLICATIONS

Asplin, J.R., D. Arsenault, J.H. Parks, F.L. Coe, and J.R. Hoyer, *Contribution of human uropontin to inhibition of calcium oxalate crystallization*. Kidney International, 1998. 53(1): p. 194-199.

De Yoreo, J.J., S.R. Qiu, and J.R. Hoyer, *Molecular modulation of calcium oxalate crystallization*. American Journal of Physiology—Renal Physiology, 2006. 291(6): p. F1123-F1131.

Guo, S.W., M.D. Ward, and J.A. Wesson, *Direct visualization of calcium oxalate monohydrate crystallization and dissolution with atomic force microscopy and the role of polymeric additives*. Langmuir, 2002. 18(11): p. 4284-4291.

Wang, L.J., W. Zhang, S.R. Qiu, W.J. Zachowicz, X.Y. Guan, R.K. Tang, J.R. Hoyer, J.J. De Yoreo, and G.H. Nancollas, *Inhibition of calcium oxalate monohydrate crystallization by the combination of citrate and osteopontin*. Journal of Crystal Growth, 2006. 291(1): p. 160-165.

Jung, T., X.X. Sheng, C.K. Choi, W.S. Kim, J.A. Wesson, and M.D. Ward, *Probing crystallization of calcium oxalate monohydrate and the role of macromolecule additives with in situ atomic force microscopy*. Langmuir, 2004. 20(20): p. 8587-8596.

Wesson, J.A., E.M. Worcester, and J.G. Kleinman, *Role of anionic proteins in kidney stone formation: Interaction between model anionic polypeptides and calcium oxalate crystals*. Journal of Urology, 2000. 163(4): p. 1343-1348.

Taller, A., B. Grohe, K.A. Rogers, H.A. Goldberg, and G.K. Hunter, *Specific adsorption of osteopontin and synthetic polypeptides to calcium oxalate monohydrate crystals*. Biophysical Journal, 2007. 93(5): p. 1768-1777.

Friddle, R.W., M.L. Weaver, S.R. Qiu, A. Wierzbicki, W.H. Casey, and J.J. De Yoreo, *Subnanometer atomic force microscopy of peptide-mineral interactions links clustering and competition to acceleration and catastrophe*. Proceedings of the National Academy of Sciences of the United States of America, 2010. 107(1): p. 11-15.

Grohe, B., B.P.H. Chan, E.S. Sorensen, G. Lajoie, H.A. Goldberg, and G.K. Hunter, *Cooperation of phosphates and carboxylates controls calcium oxalate crystallization in ultra filtered urine*. Urological Research, 2011. 39(5): p. 327-338.

Grohe, B., J. O'Young, D.A. Ionescu, G. Lajoie, K.A. Rogers, M. Karttunen, H.A. Goldberg, and G.K. Hunter, *Control of calcium oxalate crystal growth by face-specific adsorption of an osteopontin phosphopeptide*. Journal of the American Chemical Society, 2007. 129(48): p. 14946-14951.

Wang, L.J., X.Y. Guan, R.K. Tang, J.R. Hoyer, A. Wierzbicki, J.J. De Yoreo, and G.H. Nancollas, *Phosphorylation of osteopontin is required for inhibition of calcium oxalate crystallization*. Journal of Physical Chemistry B, 2008. 112(30): p. 9151-9157.

Weaver, M.L., S.R. Qiu, R.W. Friddle, W.H. Casey, and J.J. De Yoreo, *How the Overlapping Time Scales for Peptide Binding and Terrace Exposure Lead to Nonlinear Step Dynamics during Growth of Calcium Oxalate Monohydrate*. Crystal Growth & Design, 2010. 10(7): p. 2954-2959.

DeOliveira, D.B. and R.A. Laursen, *Control of calcite crystal morphology by a peptide designed to bind to a specific surface*. Journal of the American Chemical Society, 1997. 119(44): p. 10627-10631.

Long, J.R., J.L. Dindot, H. Zebroski, S. Kiihne, R.H. Clark, A.A. Campbell, P.S. Stayton, and G.P. Drobny, *A peptide that inhibits hydroxyapatite growth is in an extended conformation on the crystal surface*. Proceedings of the National Academy of Sciences of the United States of America, 1998. 95(21): p. 12083-12087.

Kim, I.W., S. Collino, D.E. Morse, and J.S. Evans, *A crystal modulating protein from molluscan nacre that limits the growth of calcite in vitro*. Crystal Growth & Design, 2006. 6(5): p. 1078-1082.

Silverman, L.D., M. Saadia, J.S. Ishal, N. Tishbi, E. Leiderman, I. Kuyunov, B. Rocca, C. Reitblat, and R. Viswanathan, *Hydroxyapatite Growth Inhibition by Osteopontin Hexapeptide Sequences*. Langmuir, 2010. 26(12): p. 9899-9904.

Elhadj, S., E.A. Salter, A. Wierzbicki, J.J. De Yoreo, N. Han, and P.M. Dove, *Peptide controls on calcite mineralization: Polyaspartate chain length affects growth kinetics and acts as a stereochemical switch on morphology*. Crystal Growth & Design, 2006. 6(1): p. 197-201.

Shiba, K. and T. Minamisawa, *A synthesis approach to understanding repeated peptides conserved in mineralization proteins*. Biomacromolecules, 2007. 8(9): p. 2659-2664.

Sheng, X.X., T.S. Jung, J.A. Wesson, and M.D. Ward, *Adhesion at calcium oxalate crystal surfaces and the effect of urinary constituents*. Proceedings of the National Academy of Sciences of the United States of America, 2005. 102(2): p. 267-272.

Graether, S.P., M.J. Kuiper, S.M. Gagne, V.K. Walker, Z.C. Jia, B.D. Sykes, and P.L. Davies, *beta-helix structure and ice-binding properties of a hyperactive antifreeze protein from an insect*. Nature, 2000. 406(6793): p. 325-328.

Doxey, A.C., M.W. Yaish, M. Griffith, and B.J. McConkey, *Ordered surface carbons distinguish antifreeze proteins and their ice-binding regions*. Nature Biotechnology, 2006. 24(7): p. 852-855.

Qiu, S.R. and C.A. Orme, *Dynamics of Biomineral Formation at the Near-Molecular Level*. Chemical Reviews, 2008. 108(11): p. 4784-4822.

Gray, J.J., *The interaction of proteins with solid surfaces*. Current Opinion in Structural Biology, 2004. 14(1): p. 110-115.

Wang, L.J., S.R. Qiu, W. Zachowicz, X.Y. Guan, J.J. DeYoreo, G.H. Nancollas, and J.R. Hoyer, *Modulation of calcium oxalate crystallization by linear aspartic acid-rich peptides*. Langmuir, 2006. 22(17): p. 7279-7285.

Azzopardi, P.V., J. O'Young, G. Lajoie, M. Karttunen, H.A. Goldberg, and G.K. Hunter, *Roles of Electrostatics and Conformation in Protein-Crystal Interactions*. Plos One, 2010. 5(2).

Qiu, S.R., A. Wierzbicki, C.A. Orme, A.M. Cody, J.R. Hoyer, G.H. Nancollas, S. Zepeda, and J.J. De Yoreo, *Molecular modulation of calcium oxalate crystallization by osteopontin and citrate*. Proceedings of the National Academy of Sciences of the United States of America, 2004. 101(7): p. 1811-1815.

Coe, F.L. and J.R. Asplin, *Stopping the Stones*. Science, 2010. 330(6002): p. 325-326.

Kawasaki, K., A.V. Buchanan, and K.M. Weiss, *Biomineralization in Humans: Making the Hard Choices in Life*, in Annual Review of Genetics2009. p. 119-142.

Daudon, M., D. Bazin, G. Andre, P. Jungers, A. Cousson, P. Chevallier, E. Veron, and G. Matzen, *Examination of whewellite kidney stones by scanning electron microscopy and powder neutron diffraction techniques*. Journal of Applied Crystallography, 2009. 42: p. 109-115.

Ouyang, H.M., S.P. Deng, J.P. Zhong, B. Tieke, and S.H. Yu, *Crystallization of calcium oxalate monohydrate at dipalmitoylphosphatidylcholine monolayers in the presence of chondroitin sulfate A*. Journal of Crystal Growth, 2004. 270(3-4): p. 646-654.

Hug, S., B. Grohe, J. Jalkanen, B. Chan, B. Galarreta, K. Vincent, F. Lagugne-Labarthet, G. Lajoie, H.A. Goldberg, M. Karttunen, and G.K. Hunter, *Mechanism of inhibition of calcium oxalate crystal growth by an osteopontin phosphopeptide*. Soft Matter, 2012. 8(4): p. 1226-1233.

Viswanathan, P., J.D. Rimer, A.M. Kolbach, M.D. Ward, J.G. Kleinman, and J.A. Wesson, *Calcium oxalate monohydrate aggregation induced by aggregation of desialylated Tamm-Horsfall protein*. Urological Research, 2011. 39(4): p. 269-282.

Liu, J.F., H.D. Jiang, and X.Y. Liu, *How does bovine serum albumin prevent the formation of kidney stone? A kinetics study*. Journal of Physical Chemistry B, 2006. 110(18): p. 9085-9089.

Hoyer, J.R., J.R. Asplin, and L. Otvos, *Phosphorylated osteopontin peptides suppress crystallization by inhibiting the growth of calcium oxalate crystals*. Kidney International, 2001. 60(1): p. 77-82.

Grohe, B., J. O'Young, A. Langdon, M. Karttunen, H.A. Goldberg, and G.K. Hunter, *Citrate Modulates Calcium Oxalate Crystal Growth by Face-Specific Interactions*. Cells Tissues Organs, 2011. 194(2-4): p. 176-181.

Hunter, G.K., J. O'Young, B. Grohe, M. Karttunen, and H.A. Goldberg, *The Flexible Polyelectrolyte Hypothesis of Protein-Biomineral Interaction*. Langmuir, 2010. 26(24): p. 18639-18646.

(56) References Cited

OTHER PUBLICATIONS

Weaver, M.L., S.R. Qiu, J.R. Hoyer, W.H. Casey, G.H. Nancollas, and J.J. De Yoreo, *Surface Aggregation of Urinary Proteins and Aspartic Acid-Rich Peptides on the Faces of Calcium Oxalate Monohydrate Investigated by in Situ Force Microscopy.* Calcified Tissue International, 2009. 84(6): p. 462-473.

Metzler, R.A., I.W. Kim, K. Delak, J.S. Evans, D. Zhou, E. Beniash, F. Wilt, M. Abrecht, J.W. Chiou, J.H. Guo, S.N. Coppersmith, and P. Gilbert, *Probing the organic-mineral interface at the molecular level in model biominerals.* Langmuir, 2008. 24(6): p. 2680-2687.

Kim, I.W., E. DiMasi, and J.S. Evans, *Identification of mineral modulation sequences within the nacre-associated oyster shell protein, n16.* Crystal Growth & Design, 2004. 4(6): p. 1113-1118.

Michenfelder, M., G. Fu, C. Lawrence, J.C. Weaver, B.A. Wustman, L. Taranto, J.S. Evans, and D.E. Morsel, *Characterization of two molluscan crystal-modulating biomineralization proteins and identification of putative mineral binding domains.* Biopolymers, 2003. 70(4): p. 522-533.

Yamamoto, Y., T. Nishimura, A. Sugawara, H. Inoue, H. Nagasawa, and T. Kato, *Effects of Peptides on CaCO3 Crystallization: Mineralization Properties of an Acidic Peptide Isolated from Exoskeleton of Crayfish and Its Derivatives.* Crystal Growth & Design, 2008. 8(11): p. 4062-4065.

Gungormus, M., H. Fong, I.W. Kim, J.S. Evans, C. Tamerler, and M. Sarikaya, *Regulation of in vitro calcium phosphate mineralization by combinatorially selected hydroxyapatite-binding peptides.* Biomacromolecules, 2008. 9(3): p. 966-973.

Collino, S., I.W. Kim, and J.S. Evans, *Identification of an "acidic" C-terminal mineral modification sequence from the mollusk shell protein Asprich.* Crystal Growth & Design, 2006. 6(4): p. 839-842.

Lakshminarayanan, R., R.M. Kini, and S. Valiyaveettil, *Investigation of the role of ansocalcin in the biomineralization in goose eggshell matrix.* Proceedings of the National Academy of Sciences of the United States of America, 2002. 99(8): p. 5155-5159.

Ajikumar, P.K., S. Vivekanandan, R. Lakshminarayanan, S.D.S. Jois, R.M. Kini, and S. Valiyaveettil, *Mimicking the function of eggshell matrix proteins: The role of multiplets of charged amino acid residues and self-assembly of peptides in biomineralization.* Angewandte Chemie-International Edition, 2005. 44(34): p. 5476-5479.

Orme, C.A., A. Noy, A. Wierzbicki, M.T. McBride, M. Grantham, H.H. Teng, P.M. Dove, and J.J. DeYoreo, *Formation of chiral morphologies through selective binding of amino acids to calcite surface steps.* Nature, 2001. 411(6839): p. 775-779.

Hendrickson, T.L., V. de Crecy-Lagard, and P. Schimmel, *Incorporation of nonnatural amino acids into proteins.* Annual Review of Biochemistry, 2004. 73: p. 147-176.

Mersich, C. and A. Jungbauer, *Generation of bioactive peptides by biological libraries.* J Chromatogr B Analyt Technol Biomed Life Sci, 2008. 861(2): p. 160-70.

Trepel, M., R. Pasqualini, and W. Arap, Chapter 4. *Screening phage-display Peptide libraries for vascular targeted peptides.* Methods Enzymol, 2008. 445: p. 83-106.

Fujiki, Y., N. Tokunaga, S. Shinkai, and K. Sada, *Anisotropic decoration of gold nanoparticles onto specific crystal faces of organic single crystals.* Angewandte Chemie-International Edition, 2006. 45(29): p. 4764-4767.

Houghten, R.A., *General-method for the rapid solid-phase synthesis of large numbers of peptides—specificity of antigen-antibody interaction at the level of individual amino-acids.* Proceedings of the National Academy of Sciences of the United States of America, 1985. 82(15): p. 5131-5135.

Geysen, H.M., R.H. Meloen, and S.J. Barteling, *Use of Peptide-Synthesis to Probe Viral-Antigens for Epitopes to a Resolution of a Single Amino-Acid.* Proceedings of the National Academy of Sciences of the United States of America-Biological Sciences, 1984. 81(13): p. 3998-4002.

Eichler, J., *Synthetic peptide arrays and peptide combinatorial libraries for the exploration of protein-ligand interactions and the design of protein inhibitors.* Comb Chem High Throughput Screen, 2005. 8(2): p. 135-43.

Beyer, M., I. Block, K. Konig, A. Nesterov, S. Fernandez, T. Felgenhauer, C. Schirwitz, K. Leibe, R.F. Bischoff, F. Breitling, and V. Stadler, *A novel combinatorial approach to high-density peptide arrays.* Methods Mol Biol, 2009. 570: p. 309-16.

Breitling, F., A. Nesterov, V. Stadler, T. Felgenhauer, and F.R. Bischoff, *High-density peptide arrays.* Mol Biosyst, 2009. 5(3): p. 224-34.

\* cited by examiner

```
SEQUENCE LISTING

<160> NUMBER OF SEQ ID NOS: 27

<210> SEQ ID NO 1
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 1

Asp Asp Asp Ala Ala Ala Ala Ala Asp Asp Asp Ala Ala Ala Ala Ala
1               5                   10                  15

Asp Asp

<210> SEQ ID NO 2
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide
```

<400> SEQUENCE: 2

Ala Ala Asp Ala Ala Ala Ala Asp Asp Ala Ala Ala Asp Ala
1               5                   10                  15

Ala Ala

<210> SEQ ID NO 3
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 3

Ala Asp Ala Ala Ala Asp Ala Ala Asp Ala Ala Asp Asp Ala Ala Asp
1               5                   10                  15

Ala Ala

<210> SEQ ID NO 4
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 4

Ala Asp Ala Ala Asp Ala Ala Asp Ala Ala Asp Ala Ala Asp Ala Ala
1               5                   10                  15

Asp Ala

<210> SEQ ID NO 5
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 5

Ala Asp Ala Ala Asp Asp Ala Ala Asp Ala Ala Asp Asp Ala Ala Ala
1               5                   10                  15

Ala Ala

<210> SEQ ID NO 6
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 6

Ala Asp Ala Ala Ala Asp Asp Asp Ala Ala Asp Ala Ala Ala Asp
1               5                   10                  15

Asp Asp

<210> SEQ ID NO 7
<211> LENGTH: 18
<212> TYPE: PRT
<213> ORGANISM: Artificial
<220> FEATURE:
<223> OTHER INFORMATION: Synthesized Calcium oxalate monohydrate inhibitory polypeptide

<400> SEQUENCE: 7

Ala Asp Ala Ala Ala Asp Asp Ala Ala Ala Ala Ala Ala Ala Ala Asp
1               5                   10                  15

Ala Ala

<210> SEQ ID NO 8
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 8

Ala Asp Ala Ala Ala Asp Asp Ala Ala Ala Asp Ala Ala Ala Ala Asp
1               5                   10                  15

Ala Ala

<210> SEQ ID NO 9
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 9

Ala Asp Ala Ala Ala Asp Asp Ala Ala Ala Asp Ala Ala Ala Asp Asp
1               5                   10                  15

Ala Ala

<210> SEQ ID NO 10
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 10

Ala Asp Ala Ala Asp Ala Ala Ala Asp Ala Ala Asp Asp Ala Ala Asp
1               5                   10                  15

Ala Ala

<210> SEQ ID NO 11
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 11

Ala Asp Ala Ala Asp Asp Ala Ala Ala Ala Ala Ala Asp Ala Ala Asp
1               5                   10                  15

Ala Ala

<210> SEQ ID NO 12
<211> LENGTH: 18
<212> TYPE: PRT
<213> ORGANISM: Artificial
<220> FEATURE:

<223> OTHER INFORMATION: Synthesized Calcium oxalate monohydrate
       inhibitory polypeptide

<400> SEQUENCE: 12

Ala Asp Asp Ala Ala Asp Ala Ala Asp Ala Ala Asp Asp Ala Ala Asp
1               5                   10                  15

Asp Ala

<210> SEQ ID NO 13
<211> LENGTH: 18
<212> TYPE: PRT
<213> ORGANISM: Artificial
<220> FEATURE:
<223> OTHER INFORMATION: Synthesized Calcium oxalate monohydrate
       inhibitory polypeptide

<400> SEQUENCE: 13

Ala Asp Ala Asp Ala Asp Ala Asp Ala Asp Ala Asp Ala Asp Ala Asp
1               5                   10                  15

Ala Asp

<210> SEQ ID NO 14
<211> LENGTH: 18
<212> TYPE: PRT
<213> ORGANISM: Artificial
<220> FEATURE:
<223> OTHER INFORMATION: Synthesized Calcium oxalate monohydrate
       inhibitory polypeptide

<400> SEQUENCE: 14

Ala Ala Glu Ala Ala Ala Ala Glu Glu Ala Ala Ala Ala Glu Ala Ala
1               5                   10                  15

Ala Ala

<210> SEQ ID NO 15
<211> LENGTH: 18
<212> TYPE: PRT
<213> ORGANISM: Artificial
<220> FEATURE:
<223> OTHER INFORMATION: Synthesized Calcium oxalate monohydrate
       inhibitory polypeptide

<400> SEQUENCE: 15

Ala Glu Ala Ala Ala Glu Ala Ala Glu Ala Ala Glu Glu Ala Ala Glu
1               5                   10                  15

Ala Ala

<210> SEQ ID NO 16
<211> LENGTH: 18
<212> TYPE: PRT
<213> ORGANISM: Artificial
<220> FEATURE:
<223> OTHER INFORMATION: Synthesized Calcium oxalate monohydrate
       inhibitory polypeptide

<400> SEQUENCE: 16

Ala Glu Ala Ala Glu Ala Ala Glu Ala Ala Glu Ala Ala Glu Ala Ala
1               5                   10                  15

Glu Ala

<210> SEQ ID NO 17
<211> LENGTH: 18
<212> TYPE: PRT
<213> ORGANISM: Artificial

```
<220> FEATURE:
<223> OTHER INFORMATION: Synthesized Calcium oxalate monohydrate
      inhibitory polypeptide

<400> SEQUENCE: 17

Ala Glu Ala Ala Ala Glu Glu Ala Ala Ala Glu Ala Ala Ala Ala Glu
1               5                   10                  15

Ala Ala

<210> SEQ ID NO 18
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 18

Ala Glu Ala Ala Ala Glu Glu Ala Ala Ala Glu Ala Ala Ala Glu Glu
1               5                   10                  15

Ala Ala

<210> SEQ ID NO 19
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 19

Ala Glu Ala Ala Glu Ala Ala Ala Glu Ala Ala Glu Glu Ala Ala Glu
1               5                   10                  15

Ala Ala

<210> SEQ ID NO 20
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 20

Ala Glu Ala Ala Glu Glu Ala Ala Ala Ala Ala Glu Ala Ala Ala Glu
1               5                   10                  15

Ala Ala

<210> SEQ ID NO 21
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 21

Ala Glu Glu Ala Ala Glu Ala Ala Glu Ala Ala Glu Glu Ala Ala Glu
1               5                   10                  15

Glu Ala

<210> SEQ ID NO 22
<211> LENGTH: 18
<212> TYPE: PRT
```

```
<213> ORGANISM: Artificial
<220> FEATURE:
<223> OTHER INFORMATION: Synthesized Calcium oxalate monohydrate
      inhibitory polypeptide

<400> SEQUENCE: 22

Ala Glu Glu Ala Glu Glu Ala Glu Glu Ala Glu Glu Ala Glu Glu Ala
1               5                   10                  15

Glu Glu

<210> SEQ ID NO 23
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 23

Ala Glu Ala Glu Ala Glu Ala Glu Ala Glu Ala Glu Ala Glu Ala Glu
1               5                   10                  15

Ala Glu

<210> SEQ ID NO 24
<211> LENGTH: 18
<212> TYPE: PRT
<213> ORGANISM: Artificial
<220> FEATURE:
<223> OTHER INFORMATION: Synthesized Calcium oxalate monohydrate
      inhibitory polypeptide

<400> SEQUENCE: 24

Glu Glu Glu Glu Glu Glu Glu Glu Glu Glu Glu Glu Glu Glu Glu Glu
1               5                   10                  15

Glu Glu

<210> SEQ ID NO 25
<211> LENGTH: 18
<212> TYPE: PRT
<213> ORGANISM: Artificial
<220> FEATURE:
<221> NAME/KEY: CA_BIND
<222> LOCATION: 2..5..8..11..14
<223> OTHER INFORMATION: Synthesized polypeptide where Xaa at positions
      2,5,8,11 and 14 may be Aspartic acid or Glutamic acid

<400> SEQUENCE: 25

Ala Xaa Ala Ala Xaa Ala Ala Xaa Ala Ala Xaa Ala Ala Xaa Ala Ala
1               5                   10                  15

Xaa Ala

<210> SEQ ID NO 26
<211> LENGTH: 18
<212> TYPE: PRT
<213> ORGANISM: Artificial
<220> FEATURE:
<221> NAME/KEY: CA_BIND
<222> LOCATION: 2...6,7...11...15,16
<223> OTHER INFORMATION: Synthesized polypeptide where Xaa at positions
      2, 6, 7, 11, 15 and 16 may be Aspartic acid or Glutamic acid

<400> SEQUENCE: 26

Ala Xaa Ala Ala Ala Xaa Xaa Ala Ala Ala Xaa Ala Ala Ala Xaa Xaa
1               5                   10                  15

Ala Ala
```

```
<210> SEQ ID NO 27
<211> LENGTH: 18
<212> TYPE: PRT
<213> ORGANISM: Artificial
<220> FEATURE:
<221> NAME/KEY: CA_BIND
<222> LOCATION: 2..5...9..12,13..16
<223> OTHER INFORMATION: Synthesized polypeptide where Xaa at positions
      2, 5, 9, 12,13, and 16 may be Aspartic acid or Glutamic acid

<400> SEQUENCE: 27

Ala Xaa Ala Ala Xaa Ala Ala Ala Xaa Ala Ala Xaa Xaa Ala Ala Xaa
1               5                   10                  15

Ala Ala
```

PEPTIDE INHIBITORS OF CALCIUM OXALATE MONOHYDRATE CRYSTALLIZATION AND USES THEREOF

RELATED APPLICATIONS

This application claims the benefit of U.S. Provisional Patent Application No. 61/844,143, filed on Jul. 9, 2013, which is incorporated herein by reference.

STATEMENT REGARDING FEDERALLY-SPONSORED RESEARCH

This invention was made with U.S. government support under grant No. 1207441 and No. 1207411 awarded by the National Science Foundation. The U.S. government may have certain rights in this invention.

BACKGROUND

Calcium oxalate is the most common constituent of urinary calculi and relatively large crystals of this salt are frequently found in freshly voided urine from patients with recurrent calcium-containing stones. Current treatments of Calcium Oxalate Monohydrate (COM) stone disease include water intake and diet supervision, which collectively reduce calcium oxalate supersaturation in urine. Hydrochlorothiazide, sodium potassium phosphate, and potassium citrate are drugs available for the treatment of calcium oxalate stone disease and reported to reduce its recurrence. While these treatments can be effective, they do not suppress stone incidence. Therefore, there is a need to develop more effective drugs for preventing calcium oxalate stone formation and to dissolve kidney stones/fragments.

SUMMARY

In some embodiments the present disclosure provides a composition for inhibiting calcium oxalate monohydrate crystal growth comprising at least one isolated polypeptide comprising a plurality of amino acids that bind the surface of the calcium oxalate monohydrate crystal; and a plurality of amino acids spacers that lack β-carbon side chains. In some embodiments the amino acid spacers are interspersed in varying sequences between the plurality of amino acids that bind the surface of the calcium oxalate monohydrate crystal.

In some embodiments, the present disclosure provides a method of controlling calcium oxalate monohydrate crystal growth in a subject in need thereof. In some embodiments, such a method comprises administering to the subject a therapeutically effective amount of at least one of the aforementioned COM inhibitory polypeptides.

In another embodiment, the present disclosure pertains to a method of identifying calcium oxalate monohydrate inhibiting peptides. In some embodiments, such a method comprises the steps of designing a peptide library of potential calcium oxalate inhibiting peptides. In a related embodiment, the method comprises screening the peptide library for high efficacy COM inhibitor peptides. In an embodiment, the method comprises conducting molecular characterization of the high efficacy inhibitor.

In an embodiment, the present disclosure relates to a method of inhibiting abnormal biomineralization in a subject in need thereof. In some embodiments, such a method comprises administering to the subject therapeutic effective amounts of at least one of the aforementioned COM inhibitory polypeptides. In some embodiments, the abnormal biomineralization causes disease selected from the group consisting of recurrent stone disease, primary hyperoxaluria, and systemic oxalosis.

The above objects and other objects, features, and advantages of the present invention are readily apparent from the following detailed description of the best mode for carrying out the invention when taken in conjunction with the accompanying drawings.

BRIEF DESCRIPTION OF THE FIGURES

In order that the manner in which the above recited and other advantages and objects of the invention are obtained, a more particular description of the invention briefly described above will be rendered by reference to specific embodiments thereof, which are illustrated in the appended Figures. Understanding that these Figures depict only typical embodiments of the invention and are therefore not to be considered limiting of its scope, the invention will be described with additional specificity and detail through the use of the accompanying Figures in which:

FIG. 2B shows a scatter plot of screened peptide inhibitors of COM crystallization, categorized in regions of low (LI, <20%), moderate (MI, 20 to 35%) and high (HI, >35%) inhibition for reducing the rate of COM crystal growth (FIG. 2B). The percent reduction in COM growth rate was calculated by comparing the ISE slopes of peptides and control using the formula, Percent Reduction=$[1-(dCa/dt)_{peptide}/(dCa/dt)_{control}] \times 100\%$. Data are averages of 2 or 3 measurements (error bars equal two standard deviations);

Figure 4:
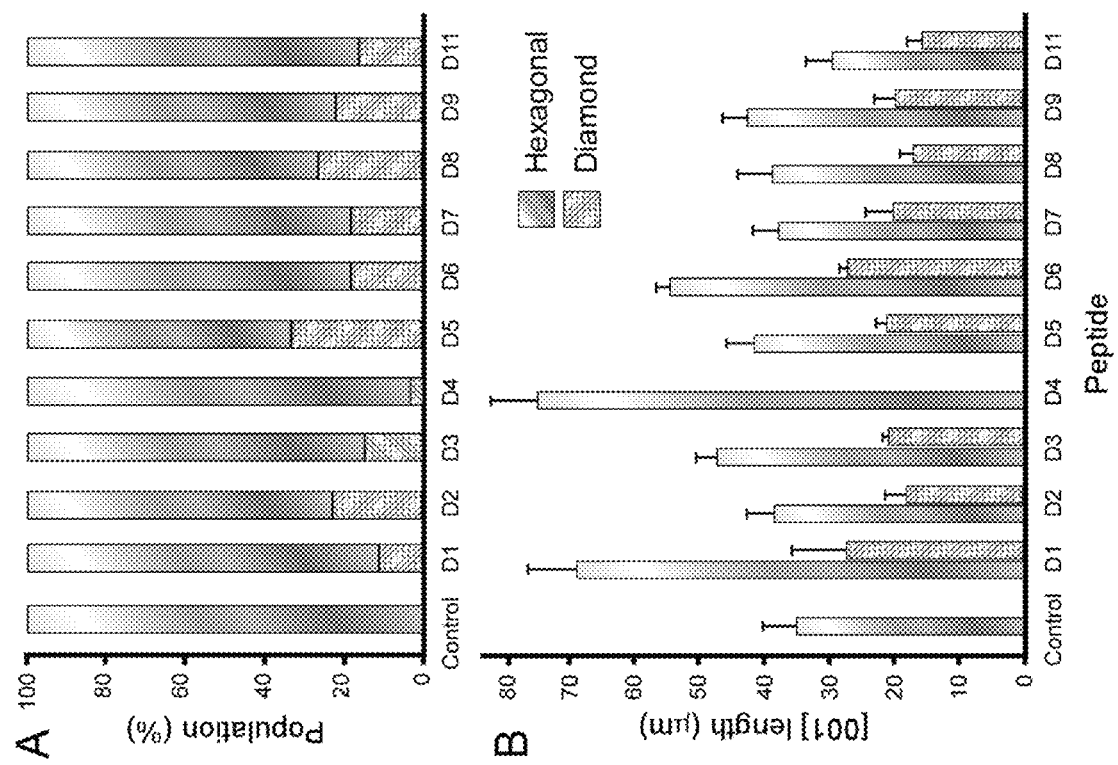
FIGS. 4A-4B show macroscopic characterization of COM crystals from bulk crystallization in solutions of 0.5 mM $CaC_2O_4$ and 20 μg/ml peptide. Optical microscopy was used to measure: Percent distribution of elongated hexagonal platelet (shaded bars) and diamond platelet (pattern bars) crystal morphologies (FIG. 4A); and length of the COM (100) basal surface measured along the [001] direction (i.e.
Figure 5:
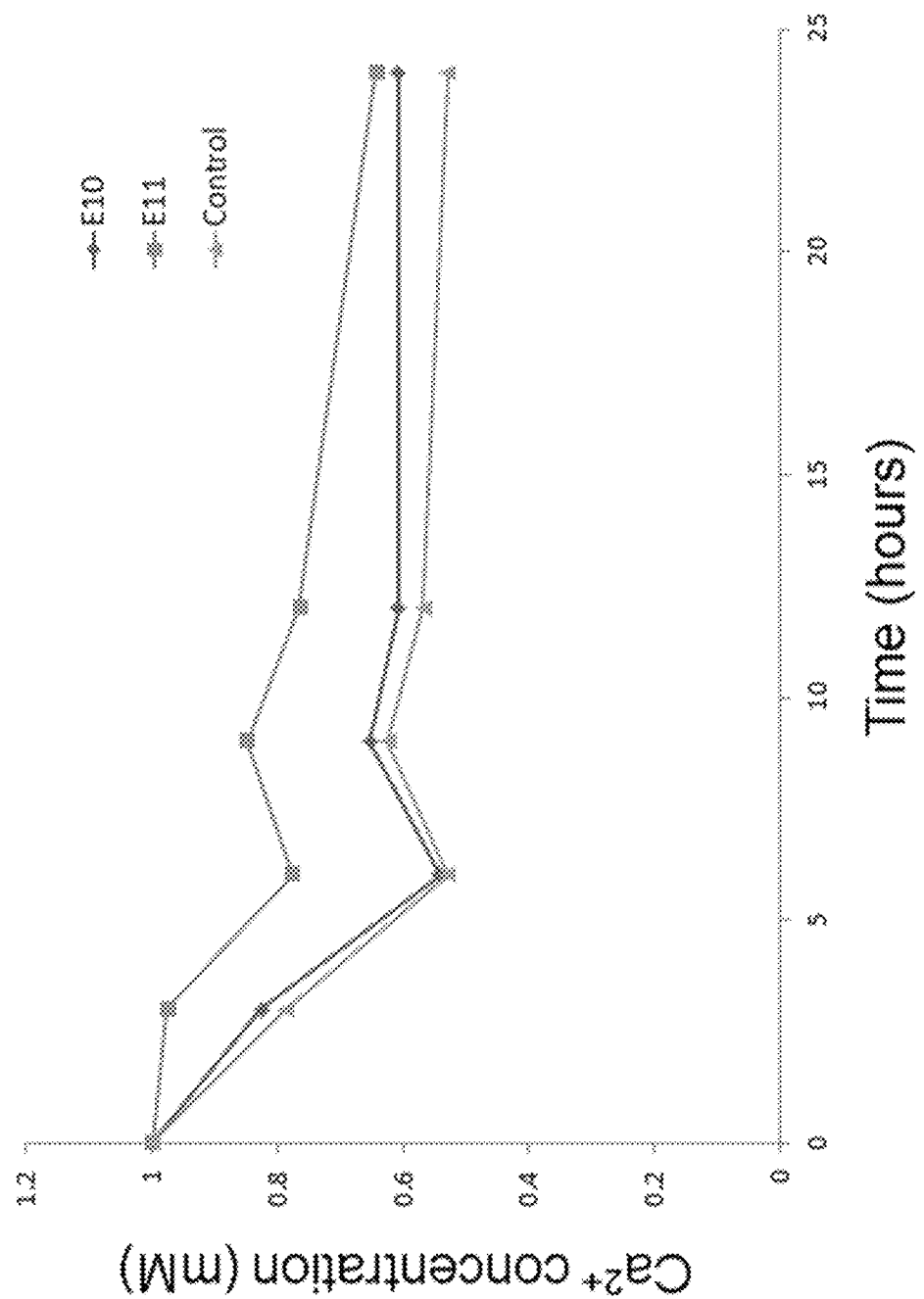
Figure 7:
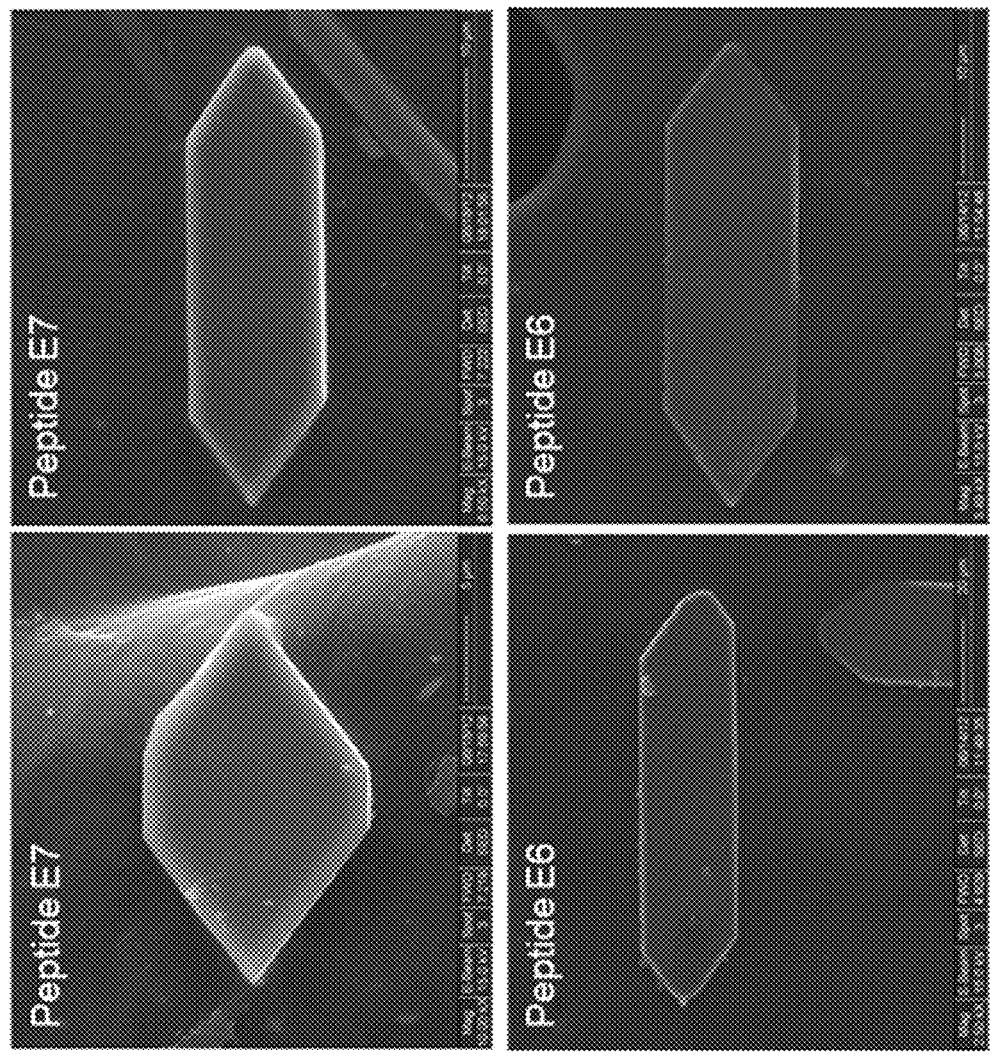
Figure 8:
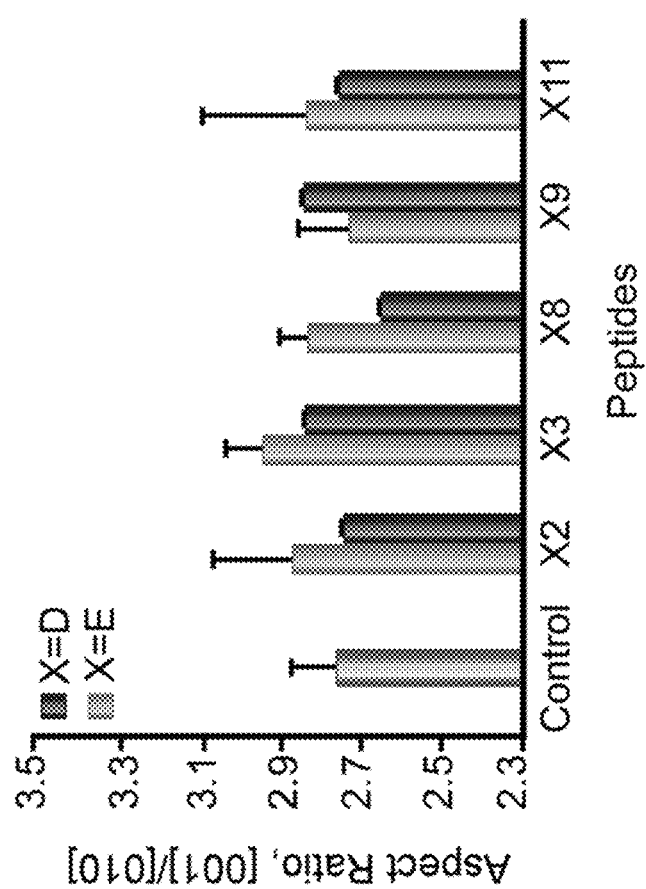

apical tip-to-tip distance) for hexagonal and diamond morphologies (FIG. 4B). Data in (FIG. 4A) and (FIG. 4B) are the average of three separate crystallization experiments performed at 60° C. for 3 days (error bars equal one standard deviation). Data for peptide D4 (diamond habit) was omitted based on too few crystals for statistical analysis;

FIG. 5 shows inhibition of COM crystal growth as evaluated by kinetic studies of COM growth at 60° C. using peptides E10 and E11 (20 μg/mL);

FIGS. 6A-6B show bulk crystallization studies of COM in presence of select peptides. Peptides E6-E10 produced COM crystals with longer dimensions as compared to control (FIG. 6A). An increased aspect ratio relative to the control was also observed with various peptides (FIG. 6B);

FIG. 7 shows a polydisperse distribution of crystals produced peptides E6 and E7. Many of the crystals possessed the elongated hexagonal shape that is characteristic of control crystals, while others had a diamond-shape that is consistent with peptide binding to surfaces. Peptide E6 was less effective than E7, as suggested by the moderate effects on crystal morphology observed in scanning electron micrographs (e.g. a rounding of the apical tips was noticed in some cases, FIG. 7); and FIG. 8 shows a comparison of the effects of Asp-Ala peptides and Glu-Ala peptides on COM crystal aspect ratio. The aspect ratio (c/b) compares the length-to-width ratio of COM platelets along the [001] and [010] directions, respectively.

DETAILED DESCRIPTION

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise. Parameters disclosed herein (e.g., temperature, time, concentration, etc.) may be approximate.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Crystallization is ubiquitous in biological systems where interactions between inorganic (salt, ions, etc.) and organic components (proteins, lipids, etc.) often mediate physiological processes in the human body, such as bone and teeth formation [1, 2]. Under abnormal physiological conditions, mineralization can lead to such pathologies as atherosclerotic plaques or vascular calcifications, kidney or gallstones, gout, and osteoarthritis. Small molecules that inhibit abnormal biomineralization are potentially effective therapies against such conditions.

Kidney stone disease is a common pathological disorder that affects more than 10-15% of the U.S. population with incidence rates that are on the rise [3, 4]. Kidney stone pathogenesis is a complex process that involves a series of steps operating either singularly or synergistically to produce polycrystalline aggregates in the kidney [5]. Calcium oxalate monohydrate (COM) is the most common component of human kidney stones. Supersaturated calcium oxalate in urine facilitates COM crystal nucleation and growth. The aggregation of COM crystals and the cumulative retention of crystals and/or aggregates in the kidney have adverse effects once stones reach an appreciable size and become dislodged from epithelial membrane. Inhibiting one or more of the critical pathways of COM stone pathogenesis nucleation, growth, aggregation, and retention via the addition of external agents can potentially serve as an effective therapy for this disease.

The rate of crystal growth and aggregation of calcium oxalate will determine whether or not a particle large enough to be trapped at some narrow point in the urinary tract can be formed within the transit time of urine through the urinary system. The chance of a particle being trapped depends partly on the size of the particle. The rate of crystal growth may also determine to a large extent the subsequent rate of growth into a stone. It has been proposed that crystal growth inhibitors possess two types of moieties, a binder that strongly interacts with crystal surface sites, and a perturber that sterically hinders the attachment of solute to crystal surfaces [6]. A common binder group of COM crystal inhibitors (i.e. urinary proteins and their synthetic analogues) is carboxylic acid, which binds to oxalate vacancies on COM crystal surfaces via calcium bridges, $_{(COM)}COO^- \ldots Ca^{2+} \ldots {}^-OOC_{(inhibitor)}$. Lahav, Leiserowitz, and coworkers [7] have proposed mechanisms of crystal growth inhibition that occur through the adsorption of small molecules to surfaces of crystals growing by classical nucleation and spreading of layers (so called layer-by-layer growth). Inhibitors that bind to different sites on a crystal surface (i.e. steps, ledges, and terraces) reduce step advancement normal to that surface. Inhibitors can therefore serve to retard crystal growth, with implications in therapies for biomineralization-based diseases, or alter growth rates of specific faces, with implications in crystal shape engineering for design of advanced materials.

There are several native proteins in urine that are putative inhibitors of COM crystal growth and/or aggregation [8, 9]. A common trait of these inhibitors is an appreciable quantity of negatively-charged amino acids, L-aspartic acid (Asp, D) and L-glutamic acid (Glu, E), and phosphorylated or glycosylated modified groups in their structure. Polymeric macromolecules have been shown to be significantly more potent inhibitors of COM crystallization than their corresponding monomers [10], which can be attributed to proximal sites on the polymer chain (e.g. carboxylic acids) that cooperatively bind to COM crystal surfaces.

Past studies have investigated COM crystallization in the presence of synthetic molecules that mimic the functional moieties of protein inhibitors found in vivo, including small organic molecules, such as citrate [11], and macromolecules, such as polyamino acids (poly-L-Asp and poly-L-Glu) and poly(acrylic) acid [12]. It has been shown that these peptides are effective in altering in vitro biomineralization [13]. For example, previous studies of COM crystallization have examined the effect of peptide mimics of urinary protein segments, notably osteopontin (OPN), and showed that the amino acid sequence plays an important role in determining peptide binding affinity to COM crystal surfaces [14]. It has been suggested that OPN-derived peptides inhibit COM growth by forming clusters or continuous films on COM crystal surfaces [15], which can promote the formation of less stable hydrates (e.g. calcium oxalate dihydrate) [16]. Additional factors affecting the inhibition of COM crystallization include peptide phosphorylation [17, 18], and the concentrations of peptide [18] and solute [19]. Similar observations have been reported for other biominerals, such as calcium carbonate [20] and calcium phosphate [21]. Studies using calcium-binding peptides rich in acidic amino acids observed that a number of properties of peptides influence crystallization, among which include peptide subdomains [22], amino acid sequence [23] and length [24], and motifs (i.e. repeating Asp and Glu patterns) [25].

Peptides are an attractive template for designing tailored crystal growth inhibitors. The modular synthesis of peptides is amenable for high-throughput analyses, and permits modifiers to be constructed with controlled size, programmable sequences, secondary structure, and stereochemical modularity whereby residues can be easily substituted to systematically alter chemical functionality and spatial proximity of recognition sites. They also allow for the rational design of physico-chemical properties, such as high solubility, high bioavailability, and low or no toxicity. Designing de novo sequences from first principles is challenging due to the vast diversity in the chemical space and number of possible sequences of peptides. High-throughput methods that allow rapid synthesis and screening of peptide libraries can significantly enhance peptide design based on rational principles.

A challenge in the rational design of inhibitors is tailoring the molecular recognition between inhibitor and crystal through the judicious selection of inhibitors with appropriate functionality, size, and structure. The present disclosure relates to the influence of chemical functionality in small peptides derived from varying sequences of Aspartic acid (Asp) and Alanine (Ala) amino acids. The rationale, philosophy and approaches of the present disclosure are translatable to design of peptide modifiers (i.e. inhibitors and promoters) of crystal growth and properties, such as crystal habit and size.

Peptides are also an attractive template for engineering chemical and structural motifs that provide effective crystal growth control. The present disclosure pertains to the efficacy of short peptide sequences (~18 amino acids in length) as effective COM crystallization inhibitors. Furthermore, the present disclosure relates to subtle changes to COM peptide inhibitor sequence that can translate into profound changes in inhibitory potential of the peptides. Additionally, the present disclosure pertains to the use of ISE-based high-throughput screening and identification of potent peptides, and their validation as effective inhibitors in bulk crystallization studies.

It is reasonable to expect that the application of the design algorithm, disclosed herein, using biomimetic peptide sequences derived from targeted segments of known calcium-binding proteins has the potential to further improve peptide performance as potent inhibitors of COM crystal growth. Furthermore, molecular-level analysis addressing fundamental aspects of peptide-crystal interactions may establish an improved understanding of structure-function properties for input into the design algorithm for refinement and testing.

The versatile approach presented here has broader applicability for a variety of inorganic and organic materials. Notably, the results disclosed herein are promising in their direct impact on kidney stone therapies. In an exemplary embodiment, the COM inhibitors disclosed herein may be used to treat the great majority of patients suffering from recurrent stone disease, since over 75% of all renal stones contain calcium oxalate. For example, the COM inhibitors may be useful to prevent formation of stones by preventing or inhibiting nucleation, growth and/or aggregation of crystals. The COM inhibitors disclosed herein may also be used to treat these patients following extracorporeal shockwave lithotripsy to help ensure passage in the urine of shattered stone particles and renal crystal deposits. The COM inhibitors of the present disclosure may also be effective in treating patients with primary hyperoxaluria (a genetic disease resulting in massive over-production of oxalic acid) many of whom suffer total loss of renal function in the early years of life. In additional embodiments, the COM inhibitors disclosed herein may have a potential use in dissolving recurrent renal stones in patients with a history of calcium oxalate stone disease. This could result in less frequent use of the lithotripter and other techniques now used to remove kidney stones. The COM inhibitors of the present disclosure may also have use in treating patients post renal transplantation in order to prevent calcium oxalate deposition in the renal graft since many of these patients have substantial body stores of calcium oxalate following long-term dialysis. Finally, it is also envisioned that the COM inhibitors may be used to treat patients suffering from systemic oxalosis, i.e., deposition of calcium oxalate crystals in many tissues of the body. The stones being treated (or the formation of which is to be prevented) may be present in the kidney, bladder and/or urinary tract. In a further embodiment, it is also possible that other forms of treatment can be used in conjunction with administration of the compound of the present invention, i.e., ultrasound treatment to break up the stones can be utilized on a patient who has been treated with the COM inhibitors disclosed herein. In a further embodiment, COM inhibitors of the present disclosure may be utilized in preventing calcification on implantable devices, prosthetics, or the like.

The COM inhibitors disclosed herein may be used for the treatment and/or prevention of calcium oxalate stone disease by administering therapeutically effective amounts of the inhibitor to a subject in need thereof. As used herein, the term "Subject" includes animals and humans requiring intervention or manipulation due to a disease state, treatment regimen or experimental design. For laboratory experiments, laboratory mammals such as rats, mice, monkeys, as well as other mammals can be used. However, the ultimately desired use is to treat human patients who suffer from calcium oxalate stone disease.

It is contemplated that the COM inhibitor peptides will be formulated into a pharmaceutical composition comprising a therapeutically effective amount of the peptides with or without a pharmaceutically acceptable carrier. The term "therapeutically effective" refers to reduction in severity and/or frequency of symptoms, elimination of symptoms and/or underlying cause, prevention of the occurrence of symptoms and/or their underlying cause, and improvement or remediation of damage. The pharmaceutically acceptable carrier may be any carrier which is non-toxic, i.e., safe for human intake and which is compatible with the COM inhibitor peptides and the desired route of administration. In a particular embodiment of the disclosure, the therapeutic or pharmaceutical composition comprises the COM inhibitor in an effective unit dosage form. As used herein, the term "effective unit dosage" or "effective unit dose" means a predetermined amount of the COM inhibitor sufficient to be effective for dissolution of calcium oxalate kidney stones in vivo or effective to prevent or reduce the degree of formation of kidney stones in vivo.

The pharmaceutical compositions may be administered orally or parenterally, including by injection, subcutaneously or used as a suppository or pessary. The only limitation on the route of administration is that the COM inhibitor should reach the kidneys in an amount effective to treat kidney stone disease. It is also contemplated that it may be desirable for the COM inhibitor to reach the urinary tract or bladder of the patient being treated.

In some embodiments the present disclosure pertains to a composition for inhibiting calcium oxalate monohydrate crystal growth. Such a composition comprises at least one isolated polypeptide comprising a plurality of amino acids that bind the surface of the calcium oxalate monohydrate crystal and a plurality of amino acids spacers. In some embodiments of the present disclosure the amino acid spacers are arranged in varying sequences between the plurality of amino acids that bind the surface of the calcium oxalate monohydrate crystal. In some embodiments the isolated polypeptide comprises at least 18 amino acids.

In some embodiments of the present disclosure the plurality of amino acids that bind to the surface of the calcium oxalate crystals comprise L Aspartic acid (D) and the plurality of amino acids spacers comprise amino acids lacking the β-carbon side chains. In some embodiments, the plurality of amino acids spacers comprise L-Alanine (A). In some embodiments, the isolated polypeptide is selected from the group consisting of the amino acid sequences DDDAAAAADDDAAAAADD (SEQ ID NO. 1), AADAAAAADDAAAADAAA (SEQ ID NO. 2), ADAAADAADAADDAADAA SEQ ID NO. 3, ADAADAADAADAADAADA (SEQ ID NO. 4), ADAAD-DAADAADDAAAAA (SEQ ID NO. 5), ADAAADDDAAADAAADDD (SEQ ID NO. 6), ADAAADDAAAAAAADAA (SEQ ID NO. 7), ADAAADDAAADAAAADAA (SEQ ID NO. 8), ADAAADDAAADAAADDAA (SEQ ID NO. 9), ADAADAAADAADDAADAA (SEQ ID NO. 10), ADAADDAAAAAADAADAA (SEQ ID NO. 11), ADD-AADAADAADDAADDA (SEQ ID NO. 12), and ADADA-DADADADADADAD (SEQ ID NO. 13).

In some embodiments the plurality of amino acids that bind to the surface of the calcium oxalate crystals comprise Glutamic acid (E) and the plurality of amino acids spacers comprise Alanine (A) amino acids. In some embodiments, the isolated polypeptide is selected from the group consisting of the amino acid sequences AAEAAAAAEEAAAAE-AAA (SEQ ID No. 14), AEAAAEAAEAAEEAAEAA (SEQ ID NO. 15), AEAAEAAEAAEAAEAAEA (SEQ ID No. 16), AEAAAEEAAAEAAAAEAA (SEQ ID No. 17), AEAAAEEAAAEAAAEEAA (SEQ ID No. 18), AEAAE-AAAEAAEEAAEAA (SEQ ID No. 19), AEAAEE-AAAAAAEAAEAA (SEQ ID No. 20), AEEAAEAAE-AAEEAAEEA (SEQ ID No. 21), AEEAEEAEEAEEAEEAEE (SEQ ID No. 22), AEAEAE-AEAEAEAEAEAE (SEQ ID No. 23), EEEEEEEEEEEEEEEEEE (SEQ ID NO. 24).

Any amino acid in the above sequences may be replaced by an isomer or analog of a conventional amino acid (e.g., a D-amino acid), non-protein amino acids, post-translationally modified amino acids, enzymatically modified amino acid, a construct or structure designed to mimic an amino acid. In an embodiment of the present disclosure a kinase can be used to phosphorylate the COM inhibitory peptide at biologically relevant sites. In a further embodiment golcosylation may be utilized. As a non-limiting example, modified terminal groups of sugar residues that are believed to be important in stone prevention, such as carboxylic acid moieties of sialic acid groups, may be utilized.

In some embodiments, the COM inhibitory peptides of the present disclosure may be glycosylated. In some embodiments, the COM inhibitory peptides of the present disclosure may be glycosylated with one or more glycans. In some embodiments, the glycans may include, without limitation, N-linked glycans, O-linked glycans, glycosaminoglycans, and combinations thereof. In some embodiments, the glycans may include carboxylic acid moieties. In some embodiments, the carboxylic acid moieties may be utilized in stone prevention.

In more specific embodiments, the COM inhibitory peptides of the present disclosure may be glycosylated with a glycan that includes a sialic acid. In some embodiments, the carboxylic acid moieties on the sialic acid may be utilized in stone prevention.

In some embodiments the COM inhibitory polypeptides further comprise at least one pharmaceutical carrier. A pharmaceutically acceptable carrier can additionally contain physiologically acceptable compounds that act, for example, to stabilize or increase the absorption of the COM inhibitory polypeptide to be administered. Such physiologically acceptable compounds include but are not limited to, for example, carbohydrates such as glucose, sucrose or dextrans; antioxidants such as ascorbic acid or glutathione; chelating agents' such as EDTA, which disrupts microbial membranes; divalent metal ions such as calcium or magnesium; low molecular weight proteins; lipids or liposomes; or other stabilizers or excipients. COM inhibitory polypeptides can also be formulated with a material such as a biodegradable polymer or a micropump that provides for controlled slow release of the molecule.

In some embodiments the present disclosure relates to a method of controlling calcium oxalate monohydrate crystal growth in a subject in need thereof. Such a method comprises administering to the subject a therapeutically effective amount of at least one of the aforementioned COM inhibitory polypeptides. A therapeutically effective amount of a COM inhibitory polypeptide to be administered is any amount deemed nontoxic but sufficient to inhibit calcium oxalate crystal growth in the subject in need thereof.

In some embodiments the at least one COM inhibitory polypeptide is selected from the group consisting of the amino acid sequences DDDAAAAADDDAAAAADD (SEQ ID NO. 1), AADAAAAADDAAAADAAA (SEQ ID NO. 2), ADAAADAADAADDAADAA SEQ ID NO. 3, ADAADAADAADAADAADA (SEQ ID NO. 4), ADAAD-DAADAADDAAAAA (SEQ ID NO. 5), ADAAADDDAAADAAADDD (SEQ ID NO. 6), ADAAADDAAAAAAADAA (SEQ ID NO. 7), ADAAADDAAADAAAADAA (SEQ ID NO. 8), ADAAADDAAADAAADDAA (SEQ ID NO. 9), ADAADAAADAADDAADAA (SEQ ID NO. 10), ADAADDAAAAAADAADAA (SEQ ID NO. 11), ADD-AADAADAADDAADDA (SEQ ID NO. 12), and ADADA-DADADADADADAD (SEQ ID NO. 13).

In some embodiments the isolated COM inhibitory polypeptide is selected from the group consisting of the amino acid sequences AAEAAAAAEEAAAAEAAA (SEQ ID No. 14), AEAAAEAAEAAEEAAEAA (SEQ ID NO. 15), AEAAEAAEAAEAAEAAEA (SEQ ID No. 16), AEAAAEEAAAEAAAAEAA (SEQ ID No. 17), AEAAAEEAAAEAAAEEAA (SEQ ID No. 18), AEAAEAAAEAAEEAAEAA (SEQ ID No. 19), AEAAEE-AAAAAAEAAEAA (SEQ ID No. 20), AEEAAEAAE-AAEEAAEEA (SEQ ID No. 21), AEEAEEAEEAEEAEEAEE (SEQ ID No. 22), AEAEAE-AEAEAEAEAEAE (SEQ ID No. 23), EEEEEEEEEEEEEEEEEE (SEQ ID NO. 24).

In some embodiments, the subject has kidney stone disorder. In some embodiments, the subject has renal calcification disorder. In some embodiments, the subject has biomineralization induced disease. In some embodiments, the method further comprises using ultrasound therapy.

In some embodiments, the present disclosure relates to a method of identifying calcium oxalate monohydrate inhibiting peptides. In some embodiments such a method comprises the steps of designing a peptide library of potential calcium oxalate inhibiting peptides. In some embodiments, the method further comprises screening the peptide library for high efficacy inhibitor peptides for inhibition of calcium oxalate monohydrate crystallization. In some embodiments the method comprises conducting molecular characterization of the high efficacy inhibitor to determine specificity.

In some embodiments of the present disclosure, the step of designing a peptide library comprises selecting an amino acid that acts as a binder to bind to the surface of the COM crystal. In some embodiments, the method further comprises selecting an amino acid that acts as a spacer to minimize the steric hindrance of the amino acid binder to COM crystal surface and synthesizing peptides by varying the number of spacer amino acids between the binder amino acids.

A COM inhibitory polypeptide of the present disclosure may be prepared or obtained by methods known in the art including, for example, purification from an appropriate biological source or by chemical synthesis. In addition to synthesis, inhibitory polypeptides may be produced, for example, by enzymatic or chemical cleavage of larger sequences. Methods for enzymatic and chemical cleavage and for purification of the resultant protein fragments are well known in the art (see, for example, Deutscher, Methods in Enzymology, Vol. 182, "Guide to Protein Purification," San Diego: Academic Press, Inc. (1990), which is incorporated herein by reference).

Following synthesis and purification, the COM inhibitory polypeptides can be modified in a physiologically relevant manner by, for example, further phosphorylation, acylation or glycosylation, using enzymatic methods known in the art.

The COM inhibitory peptide of the present disclosure can also be recombinantly expressed by appropriate host cells including, for example, bacterial, yeast, amphibian, avian and mammalian cells, using methods known in the art. Methods for recombinant expression and purification of peptides in various host organisms are described, for example, in Sambrook et al., Molecular Cloning: A Laboratory Manual, Cold Spring Harbor Laboratory, New York (1992) and in Ansubel et al., Current Protocols in Molecular Biology, John Wiley and Sons, Baltimore, Md. (1989), both of which are incorporated herein by reference. In some embodiments, the peptides are synthesized using solid-phase peptide synthesis.

In some embodiments, the step of screening the peptide library for high efficacy inhibitor peptides comprises mixing the test peptide with a supersaturated solution of calcium oxalate and measuring inhibition of growth of the COM crystal using in situ calcium ion-selective electrode measurement.

In some embodiments, the molecular level characterization of the identified peptide is by Atomic Force Microscopy, Scanning Electron Microscopy, and Optical Microscopy.

In some embodiments, the present disclosure relates to a method of inhibiting abnormal biomineralization in a subject in need thereof comprising administering to the subject therapeutic effective amounts of the aforementioned COM inhibitory polypeptides.

In some embodiments the at least one COM inhibitory polypeptide is selected from the group consisting of the amino acid sequences DDDAAAAADDDAAAAADD (SEQ ID NO. 1), AADAAAAADDAAAADAAA (SEQ ID NO. 2), ADAAADAADAADDAADAA SEQ ID NO. 3, ADAADAADAADAADAADA (SEQ ID NO. 4), ADAAD-DAADAADDAAAAA (SEQ ID NO. 5), ADAAADDDAAADAAADDD (SEQ ID NO. 6), ADAAADAAAAAAAADAA (SEQ ID NO. 7), ADAAADDAAADAAAADAA (SEQ ID NO. 8), ADAAADDAAADAAADDAA (SEQ ID NO. 9), ADAADAAADAADDAADAA (SEQ ID NO. 10), ADAADDAAAAAADAADAA (SEQ ID NO. 11), ADD-AADAADAADDAADDA (SEQ ID NO. 12), and ADADA-DADADADADADAD (SEQ ID NO. 13).

In some embodiments the isolated COM inhibitory polypeptide is selected from the group consisting of the amino acid sequences AAEAAAAAEEAAAAEAAA (SEQ ID No. 14), AEAAAEAAEAAEEAAEAA (SEQ ID NO. 15), AEAAEAAEAAEAAEAAEA (SEQ ID No. 16), AEAAAEEAAAEAAAAEAA (SEQ ID No. 17), AEAAAEEAAAEAAAEEAA (SEQ ID No. 18), AEAAE-AAAEAAEEAAEAA (SEQ ID No. 19), AEAAEE-AAAAAAEAAEAA (SEQ ID No. 20), AEEAAEAAE-AAEEAAEEA (SEQ ID No. 21), AEEAEEAEEAEEAEEAEE (SEQ ID No. 22), AEAEAE-AEAEAEAEAEAE (SEQ ID No. 23), EEEEEEEEEEEEEEEEEE (SEQ ID NO. 24).

In some embodiments, the abnormal biomineralization causes disease selected from the group consisting of recurrent stone disease, primary hyperoxaluria, and systemic oxalosis.

ADDITIONAL EMBODIMENTS

Reference will now be made to various embodiments of the present disclosure and experimental results that provide support for such embodiments. Applicants note that the disclosure herein is for illustrative purposes only and is not intended to limit the scope of the claimed subject matter in any way.

EXAMPLE 1

COM crystals for bulk crystallization studies were synthesized using a reported procedure that produces micron-sized crystals with large basal (100) surfaces. COM crystals prepared with molar composition 0.7 mM $CaCl_2$: 0.7 mM $Na_2C_2O_4$: 150 mM NaCl are referred to as the control. Growth solutions prepared with peptides used 20 μg/ml of the additive (unless otherwise stated). The crystals were characterized by optical microscopy using a Leica DM2500-M microscope, scanning electron microscope (SEM) using a FEI 235 Dual-Beam Focused Ion-beam instrument, atomic force microscopy (AFM) using an Asylum MFP-3D-SA instrument (Santa Barbara, Calif.), and a calcium ion-selective electrode (ISE, ThermoScientific).

Peptides were synthesized on an automated peptide synthesizer (Multipep RS, Intavis Inc., Germany). Using solid-phase peptide synthesis (SPSS) chemistry, peptides were synthesized from their C-termini to N-termini on tentagel amide resin (Intavis Inc.). Post synthesis, the peptides were cleaved from the resin. Post-cleavage, the peptides were lyophilized and stored as dry and lyophilized powders for subsequent use.

EXAMPLE 2

Designing a Peptide Library for Screening COM Growth Inhibitors

Peptides provide a unique template for designing COM growth inhibitors due to an unparalleled ability to synthesize sequences with controlled size, chemical functionality, spatial patterning, and secondary structure. De novo peptides can be designed and tested, although the infinite number of combinations calls for a more rational approach to select lead candidates. To this end, Applicants searched for inspiration among proteins that mediate biomineralization of calcium crystals (oxalates, carbonates, and phosphates). Calcium-binding proteins tend to be rich in L-aspartic acid (Asp, D) and L-glutamic acid (Glu, E), but exhibit a wide variety of primary amino acid sequences with different periodicity (e.g. XDX, XDDX, XDDDX, etc.) that cannot be uniquely identified a priori as being the most effective for COM crystal inhibition. As such, Applicants used a simple design for creating a peptide library employing one binder, L-Asp, and one spacer (perturber), L-Ala. The selection of the binder was based on a general observation that protein inhibitors of COM are rich in Asp and Glu. Applicants chose Asp for these studies as a representative example. Ala was chosen as a spacer (perturber) based on the lack of β-carbons (i.e. small side group, $R=CH_3$) to minimize steric hindrance of L-Asp binding to COM surfaces. Moreover, the hydrophobic residue of Ala may promote peptide-COM binding via entropic effects wherein oriented water molecules surrounding the methyl group are released when Ala orients on a COM crystal surface. This effect has been proposed for antifreeze protein (AFP) inhibition of ice crystallization in cold-weather species (e.g. fish, plants, and insects) [27]. In brief, AFPs contain many Thr groups with H-binding residues that promote AFP-ice adhesion. It has been suggested that Ala groups (located in close proximity to Thr) are a secondary binder that promote AFP adsorption via an entropic effect attributed to the release of unfavorable hydration layers when hydrophobic $CH_3$ groups bury into vacancies on ice surfaces [28].

Table 1 lists the peptide sequences selected for these studies (named D1 to D13), which represent combinations of randomly selected Ala-Asp sequences. Some of these peptides possess similar XDX, XDDX, and XDDDX, patterns with subtle changes, such as the removal or addition of a single binder or spacer group. This library was used as an initial test for the design approach to synthesize and screen effective inhibitors of COM crystallization. Details of the design platform and experimental screening of this peptide library are presented in the following sections.

EXAMPLE 2

High-Throughput Platform for Screening Peptide Inhibitors

Figure 1:
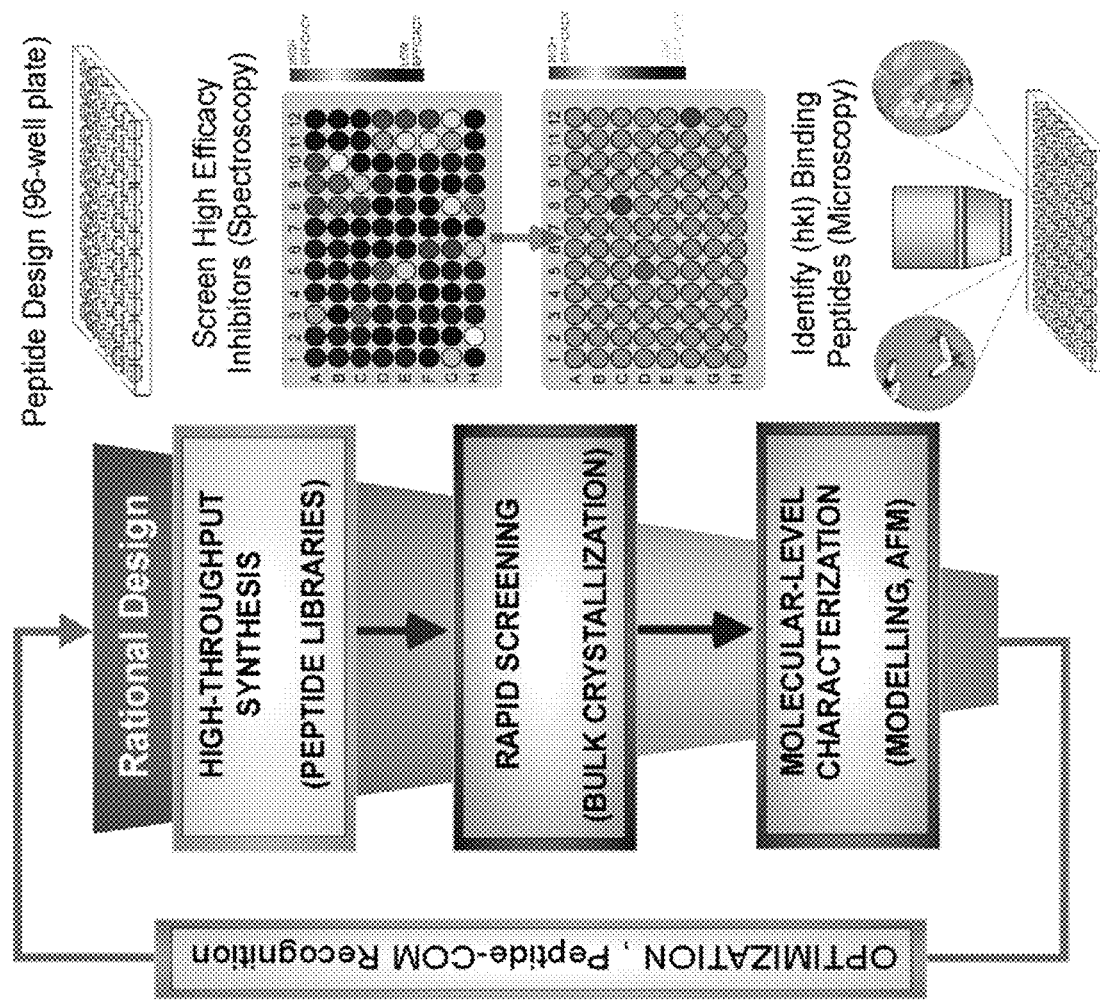
FIG. 1 shows a rational approach to design and screen peptides as inhibitors of COM crystallization using a high-throughput scheme to synthesize and screen peptide libraries, characterize peptide inhibitor specificity at the molecular level (e.g. using modeling, AFM, etc.) for the most promising candidates, and apply information gained from systematic studies of peptide inhibition for designing new sets of peptide libraries.

The schematic in FIG. 1 outlines the high-throughput platform proposed here for the design, testing, and modeling of peptide inhibitors of COM crystallization. This sequential approach employs facile analytical methods to rapidly quantify macroscopic changes in COM crystal growth rate and bulk crystal habit. Techniques used in this study monitor the temporal evolution of $Ca^{2+}$ supersaturation during COM growth and the final bulk crystal morphology, which permits fast and reproducible assessment of peptide specificity and efficacy. The overarching goal of the design platform in FIG. 1 is to refine large libraries of peptides to a list of the most effective inhibitors for molecular-level studies of peptide-crystal interactions that are typically time and effort intensive. These include, for instance, scanning force microscopy [29] and molecular modeling [30] that have proven effective for investigating adsorbate interactions at solid-liquid interfaces. Applicants anticipate that the application of this high-throughput platform in future COM studies will provide valuable information of peptide-crystal molecular recognition as an input for the design of new libraries. This process of peptide synthesis, screening, and systematic studies constitutes an iterative optimization loop wherein molecular-level investigation of select inhibitors can be used to develop heuristic guidelines for further design and refinement of peptide inhibitors.

EXAMPLE 3

Screening the Peptide Library for High Efficacy Inhibitors of COM

Figure 2:
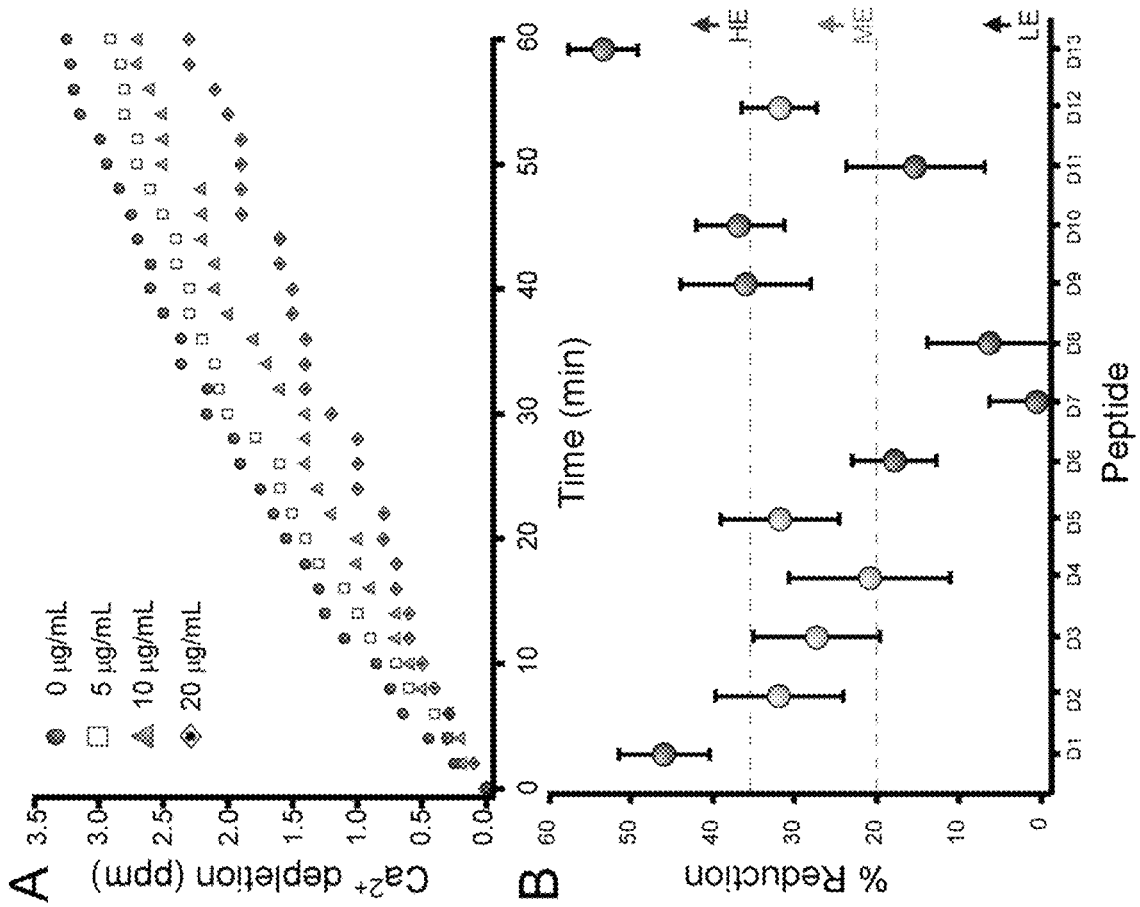
FIGS. 2A-2B show $Ca^{2+}$ ion-selective electrode (ISE) measurements of COM crystallization with peptide D1 at different concentrations (FIG. 2A). The COM growth rate was measured as the slope (dCa/dt) of decreasing $Ca^{2+}$ concentration within the first 40 min of crystallization.

A quantitative comparison of peptide efficacy for inhibiting COM crystallization was performed using in situ calcium ion-selective electrode (ISE) measurements. Supersaturated solutions of calcium oxalate (S=5.4) with peptide (20 μg/ml) were stirred to minimize the induction period of crystal nucleation (observed times ranged from 0 to 20 min with stirring). The temporal depletion of $Ca^{2+}$ (ppm) during COM growth is approximately linear within the first hour of measurement, as shown in FIG. 2A for ISE potency measurements of COM crystallization at varying concentrations of test peptide D1. This study revealed that 20 μg/ml peptide in COM growth solutions was sufficient to observe COM

TABLE 1

Peptide library synthesized for high-throughput studies of COM growth inhibition.

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| D1 | D | D | D | A | A | A | A | A | D | D | D | A | A | A | A | A | D | D |
| D2 | A | A | D | A | A | A | A | A | D | D | A | A | A | D | A | A | A | A |
| D3 | A | D | A | A | A | D | A | A | D | A | A | D | D | A | A | D | A | A |
| D4 | A | D | A | A | D | A | A | D | A | A | D | A | A | D | A | A | D | A |
| D5 | A | D | A | A | D | D | A | A | D | A | A | D | D | A | A | A | A | A |
| D6 | A | D | A | A | A | D | D | D | A | A | A | D | A | A | A | D | D | D |
| D7 | A | D | A | A | A | D | D | A | A | A | A | A | A | A | D | A | A | A |
| D8 | A | D | A | A | A | D | D | A | A | A | D | A | A | A | A | D | A | A |
| D9 | A | D | A | A | A | D | D | A | A | A | D | A | A | A | D | A | A | A |
| D10 | A | D | A | A | D | A | A | A | D | A | A | D | D | A | A | D | A | A |
| D11 | A | D | A | A | D | D | A | A | A | A | A | A | D | A | A | D | A | A |
| D12 | A | D | D | A | A | D | A | A | D | A | A | D | D | A | A | D | D | A |
| D13 | A | D | A | D | A | D | A | D | A | D | A | D | A | D | A | D | A | D | growth inhibition with statistical certainty. As such, measurements reported herein were conducted at a single peptide concentration (20 µg/ml) to assess COM growth inhibition. To facilitate comparison of peptides in Table 1, Applicants calculated the percent reduction in COM growth rate using the relative difference in ISE slopes (units of ppm $Ca^{2+}$ per time) for peptide and control samples during the first 40 min of crystallization. A scatter plot of ISE results in FIG. 2B reveals a large distribution of peptide efficacy spanning 0.6 to 58% reduction in COM growth rate.

Some of the most potent inhibitors of COM reported by other groups are macromolecules, such as OPN or poly (aspartic) acid, which reduce COM growth by >90% [12]. Small molecules generally tend to be less effective inhibitors of COM crystallization. A notable exception is citrate, which is a small organic molecule with three carboxylic acid groups. Citrate is a moderately effective inhibitor used as an oral therapy for human stone disease [11]. Here Applicants analyzed citrate as a benchmark for determining the relative effectiveness of peptides as COM growth inhibitors. ISE measurements of COM crystallization with 20 µg/ml citrate yielded a 28±6% reduction in COM growth rate, which is comparable to the average percent inhibition observed for all peptides in Table 1. Interestingly, more than 30% of the peptides performed better than citrate in this small library based on crude design principles. Using the results of citrate as a reference point, Applicants subdivided data in FIG. 2B into three regions of low (LI), moderate (MI), and high (HI) inhibition, where the threshold for an effective inhibitor was defined as any peptide exhibiting >35% reduction in COM growth rate (i.e. statistically higher than citrate), and those with low efficacy exhibiting <20% reduction.

Inhibitor performance from ISE screening should be evaluated within the context of COM growth conditions—notably temperature, calcium oxalate supersaturation, inhibitor concentration, and ionic strength. It is important to mention that ISE, while shown here to be an effective method for quickly and reproducibly screening large peptide libraries, does have its limitations for assessing COM crystallization for detailed kinetic studies near equilibrium. The sensitivity of ISE electrodes necessitates the use of high (non-physiological) calcium oxalate concentration. Many groups have focused on COM growth (with and without inhibitors) using $CaC_2O_4$ concentrations near equilibrium. For instance, Wang et al. reported 48% reduction in COM growth rate using a similar citrate concentration as our study, but much lower supersaturation (S=1.3) [11]. It is reasonable to expect that high efficacy peptides identified in ISE analyses may exhibit more pronounced inhibition of COM growth rates at lower supersaturation (i.e. conditions that mimic COM crystallization in vivo).

The slope of ISE curves (FIG. 2A) is the temporal change in free $Ca^{2+}$ concentration due to COM nucleation (primary and secondary) and crystal growth. Deconvoluting these two processes (nucleation and growth) from ISE data is non-trivial, particularly if one wishes to extract detailed kinetic information of COM growth rates. To this end, Applicants suggest using an alternative approach, such as the constant composition (CC) method pioneered by Nancollas and coworkers [18]. In the current study, the distinct advantage of ISE compared to more traditional approaches is its ease of use and the rapid time for data acquisition that enables high-throughput analysis of large peptide libraries.

EXAMPLE 4

Influence of Peptide Sequence on COM Growth Inhibition

Close inspection of trends in FIG. 2B reveals a nontrivial relationship between peptide efficacy and its sequence (Table 1). Elucidating the mechanism of peptide-COM recognition would require the use of more sophisticated techniques (e.g. molecular simulations, scanning probe microscopy, etc.) to probe molecular-level details of peptide interactions with COM crystal surfaces. The goal of this study is to validate a platform capable of screening a large number of potential growth inhibitors in a reasonably short period of time to identify "hits" for more systematic, fundamental studies. Without a mechanistic understanding of peptide-crystal molecular recognition, it is difficult to draw definitive conclusions here. Nevertheless, there are several interesting observations in FIG. 2B that emphasize how subtle changes in peptide sequence influence its efficacy as a COM growth inhibitor. In comparing peptides D4, D5, and D9, which contain identical numbers of L-Asp groups but different sequences, Applicants observe that the arrangement of L-Asp groups has a pronounced effect on the percent reduction in COM growth rate. The ADA sequence of peptide D4 yielded a 20% reduction in COM crystal growth. The rearrangement of binders to generate a mixture of D and DD sequences (peptide D5) increased the percent reduction to 30%; and further alteration of this sequence by inserting one L-Ala spacer between each D or DD group (peptide D9) further enhanced peptide efficacy to achieve a 40% reduction in COM growth. If Applicants also compare the results of peptides D7, D8, and D9, it was observed that the sequential replacement of one L-Ala spacer with one L-Asp binder increased peptide efficacy by a factor of ~70. Among the library of peptides in Table 1, peptide D7 was the least effective inhibitor of COM crystallization (<1% reduction in COM growth). Substitution of an L-Ala with L-Asp at the $11^{th}$ amino acid position yields peptide D8, which exhibited an order of magnitude increase in efficacy (~6% reduction). A second substitution at the $15^{th}$ amino acid position yielded peptide D9, which exhibited an even further increase in efficacy (~40% reduction).

Designing peptide inhibitors from de novo principles is challenging. For instance, an extensive study of an 18-mer peptide using all natural amino acids would be virtually impossible. An exhaustive study of all unique 18-mer sequences derived from a library of only L-Asp and L-Ala amino acids would require screening a smaller, but still substantially large, library of more than $10^5$ peptides. A more rational approach would be the use of sequences from known protein inhibitors of COM crystallization as a starting point for peptide design. Indeed, past studies by DeYoreo [31] and Hunter [14] identified potent inhibitors of COM growth using peptide mimics of OPN segments. DeYoreo and coworkers examined COM growth in the presence of 27-mer peptides with repeating DDDX sequences (where X=Ser or Gly space groups). They reported a 90% reduction in COM growth using peptide concentrations of 0.02 µg/ml (X=Gly) and 2.2 µg/ml (X=Ser), where the 30-fold increase in peptide potency was achieved by simply switching the spacer from glycine (R group=H) to serine (R group=$CH_2OH$). DeYoreo and Hunter also tested smaller 14-mer [18] and 16-mer [32] segments of OPN, respectively, and showed that phosphorylation of primary amino acid sequences can achieve more than 60% reduction in COM growth.

EXAMPLE 5

Bulk Crystallization Studies to Assess Peptide-COM Specificity

Figure 3:
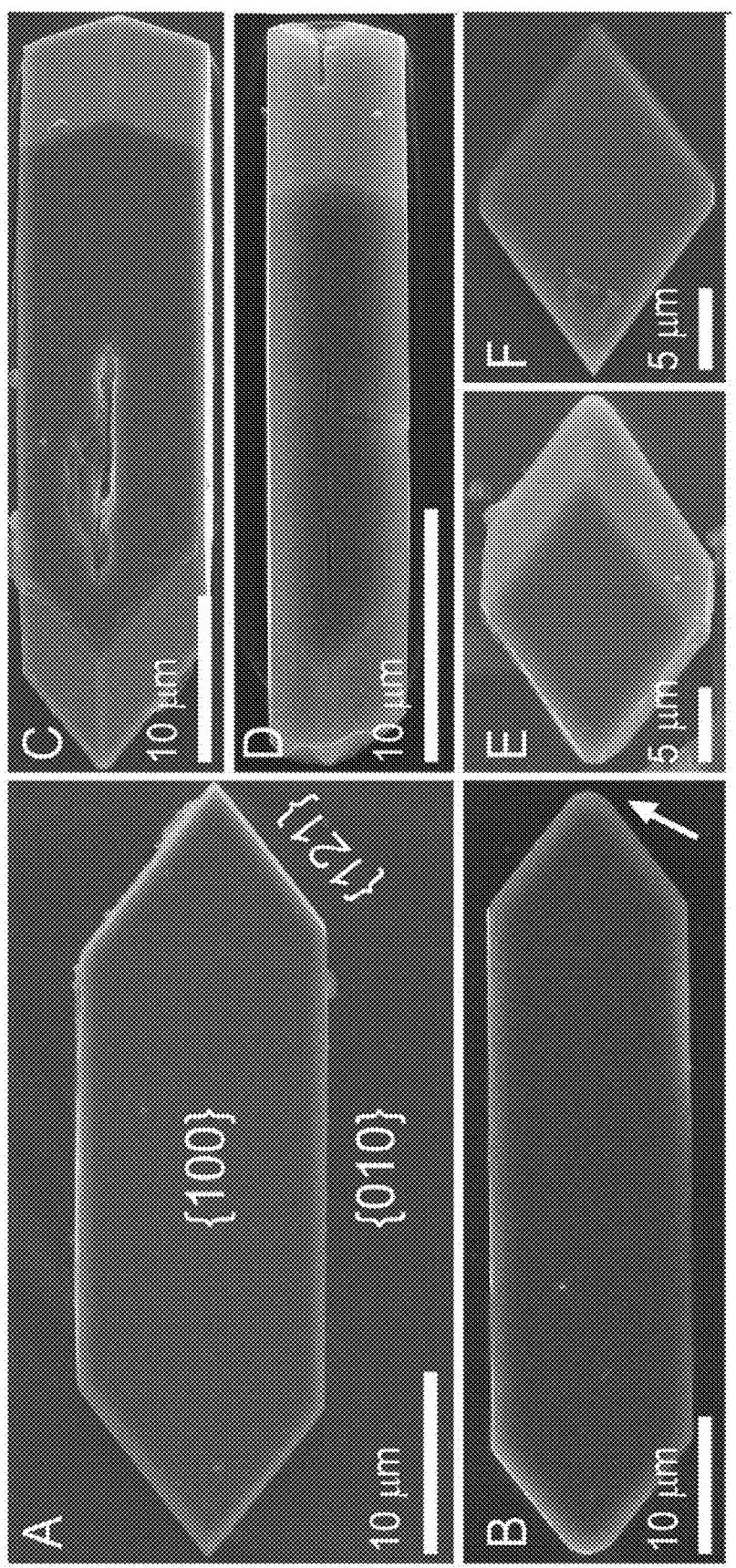
FIGS. 3A-3F show SEM images of COM crystals from bulk crystallization in the presence of 20 μg/ml peptide inhibitors of the present disclosure. Control crystals (no peptide additive) exhibit an elongated hexagonal platelet morphology with basal {100} surfaces bounded by {010} and {121} sides (FIG. 3A). COM crystals prepared with peptide D4 exhibit higher length-to-width aspect ratio (FIG. 3B). Several peptides in the library also induced rounding of the apical tip (arrow in B). Images taken normal to the {010} plane permit a comparison of COM {100} thickness among samples. It was observed that the control (FIG. 3C) has approximately twice the thickness as test peptide D7 (FIG. 3D). Peptides that bind to {121} surfaces produce diamond-shaped crystals with (FIG. 3E) large {121} surface area and (FIG. 3F) small {121} surface area (shown for COM crystals prepared using peptides D11 and D1, respectively)

ISE measurements can be used to screen peptide efficacy, but provide little information regarding the specificity of peptide binding to different surfaces of COM crystals. To this end, Applicants used a second analysis step to identify the effect of peptides on COM crystal size and habit. The influence of the peptide library on macroscopic properties of COM crystals was assessed using bulk crystallization studies and optical and scanning electron microscopy to characterize COM crystals grown in the presence of peptides. In vitro, COM crystallization yields elongated hexagonal platelets with {100} basal surfaces bounded by {010} and crystallographically equivalent {121} apical surfaces (FIG. 3A). Crystals prepared in the absence of peptide (control, FIG. 3A) exhibit basal surfaces with a ~35 μm length along the axis, ~13 μm width along the [010] axis, and a thickness of ~9 μm along the [100] axis (see FIG. 3C). Applicants observed that multiple peptides in the library reduced growth along the [121] directions, which decreased the crystal aspect ratio (length-to-width) and shifted the morphology from hexagonal to diamond platelets. This change in crystal habit can be attributed to the preferential binding of peptides to COM {121} surfaces, which slows growth along the naturally fast growth directions within the (100) plane. This result is qualitatively consistent with the reduced growth rates reported in Section 3.3.

Two distinct crystal habits of diamond shape were observed in bulk crystallization studies. The most commonly observed shape had large {121} surface area (FIG. 3D), while the least common shape had smaller {121} surface area (FIG. 3E) that closely matched the control. Interestingly, peptide-COM interactions did not significantly roughen basal (100) surfaces, as might be expected from past studies of inhibitor-COM interactions [33]. To more systematically assess the surface topography of COM crystals, Applicants used atomic force microscopy (AFM) to probe the effect of peptides on COM (100) surface roughness. Crystals extracted from control and peptide D5 batches were prepared on AFM sample disks and imaged in air. The RMS roughness for (100) surfaces of hexagonal-shaped crystals from the control and test peptide D5 were approximately 1.0 and 4.3 nm, respectively. The RMS roughness of diamond-shaped crystals from the peptide study was 3.2 nm, which is comparable to the hexagonal crystal for peptide D5, but larger than the control. Despite the increase in RMS roughness, AFM images (not shown) revealed little difference in surface topography of crystals prepared with and without peptide.

Electron micrographs revealed that select peptides from the library in Table 1 reduced the [100] thickness of COM crystals, which suggests a preferential interaction of these peptides with the COM {100} surface. Notably, peptide D7 decreased the [100] thickness of hexagonal platelets by nearly a factor of two (FIG. 3D), while most other peptides had only marginal effect on platelet thickness. Another interesting observation was that a majority of the peptides induced rounding of the apical tip formed by the intersection of {121} planes (arrow in FIG. 3B) on hexagonal platelets. The SEM image in FIG. 3B is a representative example of tip rounding, although in select cases Applicants did observe more pronounced rounding than shown here.

COM crystals prepared from peptide solutions were divided into two populations based on their habit—diamond and hexagonal platelets—where the relative percentage of diamond-shaped crystals is related to peptide efficacy and specificity for binding to COM {121} surfaces. FIG. 4A compares the percentage of diamond and hexagonal COM crystals for the peptide library (data for each peptide is an average of three separate bulk crystallization experiments). All peptides produced diamond-shaped crystals, but the majority exhibited less than 20% diamonds in their total crystal population. Peptides D5 and D8 exhibited the largest populations of diamond-shaped crystals, which suggests these peptides bind more effectively to COM {121} surfaces and inhibit growth along the [121] directions. Applicants tested the effect of doubling the concentration of peptide D8 (i.e. increasing the concentration from 20 to 40 μg/ml), but Applicants did not observe an appreciable increase in the population of diamond crystals.

Crystal batches prepared in bulk studies were analyzed using optical microscopy to quantify changes in COM crystal size and aspect ratio. Diamond-shaped COM crystals exhibited an average [001] length of ~20 μm and a length-to-width aspect ratio of 1.63±0.05, which is smaller than the aspect ratio of control crystals (2.67±0.05). Although there were clear differences in the percent population of diamond-shaped crystals among peptides tested in this study, Applicants observed that the size of diamond crystals were generally the same, irrespective of peptide sequence (FIG. 4B). The majority of COM hexagonal platelets in peptide samples had similar size and aspect ratio as the control (here Applicants only report the length of COM crystals in FIG. 4B). A notable exception, however, was peptide D4, which produced a 22% increase in the length-to-width aspect ratio of COM hexagonal crystals, and an increase in the [001] length from 35 μm (control) to 75 μm (peptide D4). This suggests that peptide D4 exhibits a preferential interaction with COM (010) surfaces. To a lesser extent, peptides D6 and D1 also increased the [001] length of hexagonal COM crystals by factors of 1.5 and 2.0, respectively, relative to the control.

The embodiments described herein are to be construed as illustrative and not as constraining the remainder of the disclosure in any way. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

EXAMPLE 6

Design of Peptides with Glutamic Acid Binding Moieties

A second library of peptides containing glutamic acid (E) and alanine (A) amino acids was synthesized. The sequences of E-peptides shown in Table 2 were used in bulk crystallization studies and kinetic studies to assess their role as growth inhibitors or promoters of COM crystallization. Glutamic acid possesses a carboxylic acid group that can form a calcium bridge with surface oxalate groups of COM crystals. Calcium ISE measurements of COM growth at room temperature in the presence of peptides E3, E5, and E6 revealed a percent inhibition in the range 30 to 50% (see Table 2). Kinetic studies of COM growth at 60° C. using peptides E10 and E11 (20 μg/mL) also revealed inhibition of COM crystal growth (FIG. 5). These analyses were performed using the calcium assay to track the kinetics of crystallization over a 24-hour period. The calcium ion concentration in the supernatant solution was assessed at periodic times. Peptide E10 was a more effective inhibitor than E11.

Figure 6:
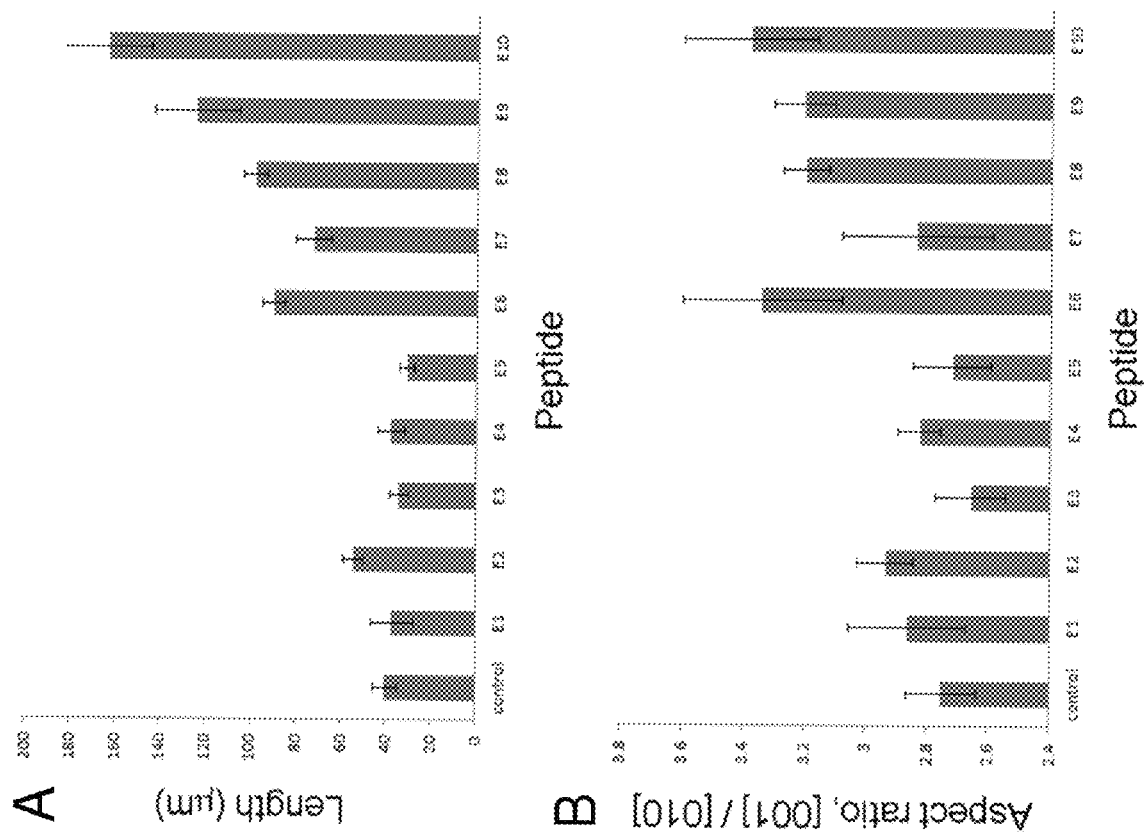

Bulk crystallization studies of COM in the presence of select peptides revealed that many E-peptides preferentially bind to the {121} surfaces of COM crystals. This results in an increase in the [001]/[010] aspect ratio relative to the control (FIG. 6). Peptides E6 to E10 produced COM crystals with longer [001] dimensions than control crystals. Moreover, the peptides produced a polydisperse distribution of crystals, as shown in FIG. 7 for peptides E6 and E7. Many of the crystals possessed the elongated hexagonal shape that is characteristic of control crystals, while others had a diamond-shape that is consistent with peptide binding to {121} surfaces. Peptide E6 was less effective than E7, as suggested by the moderate effects on crystal morphology observed in scanning electron micrographs (e.g. a rounding of the apical tips was noticed in some cases, FIG. 7).

TABLE 2

Peptide library synthesized with glutamic acid (E) and alanine (A) amino acids.

| Peptide | Sequence | % Inhibition |
|---|---|---|
| E1 | A-A-E-A-A-A-A-A-E-E-A-A-A-A-E-A-A-A | |
| E2 | A-E-A-A-A-E-A-A-E-A-A-E-E-A-A-E-A-A | |
| E3 | A-E-A-A-E-A-A-E-A-A-E-A-A-E-A-A-E-A | 40 ± 17 |
| E4 | A-E-A-A-A-E-E-A-A-A-E-A-A-A-A-E-A-A | |
| E5 | A-A-A-A-E-E-A-A-A-E-A-A-A-E-E-A-A-A | 36 ± 21 |
| E6 | A-E-A-A-E-A-A-A-E-A-A-E-E-A-A-E-A-A | 52 ± 16 |
| E7 | A-E-A-A-E-E-A-A-A-A-A-E-A-A-E-A-A | |
| E8 | A-E-E-A-A-E-A-A-E-A-A-E-E-A-A-E-A | |
| E9 | A-E-E-A-E-A-E-E-A-E-E-A-E-E-A-E-E | |
| E10 | A-E-A-E-A-E-A-E-A-E-A-E-A-E-A-E-A-E | |
| E11 | E-E-E-E-E-E-E-E-E-E-E-E-E-E-E-E-E-E | |
| Control | — | 0.00 |

EXAMPLE 7

Colorimetric Calcium Depletion Assay

Free calcium concentration in the crystallization solution was measured by a colorimetric assay using Quantichrome DICA 500 Calcium assay kit (BioAssay Systems, Hayward, Calif.). Standard solutions (0, 0.1, 0.2, 0.3, 0.4, 0.5, and 1 mM) were prepared using calcium solutions provided with the kit. Detection reagent was prepared by mixing equal volumes of reagent A and reagent B according to manufacturer's instructions. A 10 μL sample was withdrawn from the top of each crystallization well without disturbing the bottom and dispensed into a 96-well microplate. 100 μL of detection reagent was added to each well and incubated for 3 minutes at room temperature. The absorbance was measured at 612 nm using Biotek Synergy H4 microplate reader (BioTek, Winooski, Vt.). Calcium concentration was determined using a calibration curve prepared from standard calcium solutions.

EXAMPLE 8

Evaluation of Crystal Growth Modifying Potential

Time course of depletion of free calcium in the crystallization solution, normalized to the initial concentration, was fitted to a nonlinear logistic function using OriginPro Software (Origin Lab, Northhampton, Mass.). The logistic function relating calcium concentration to time is given by $$[Ca]_t = A_2 + \frac{A_1 - A_2}{1 + \left(\frac{t}{t_{1/2}}\right)^p} \quad (1)$$

where $[Ca]_t$ is the normalized calcium concentration at time t, $A_1$ is the normalized initial supersaturation concentration (i.e at t=0), $A_2$ is the normalized equilibrium concentration (i.e. at t=∞), p is the hill coefficient which represents slope of the curve at midpoint, and $t_{1/2}$ is the crystallization half-time (CHT), defined as the time at which crystallization is 50% complete (i.e. $[Ca]_{t^{1/2}}=(A_1-A_2)/2$). $A_1$ was fixed at 1, and $A_2$, p and $t_{1/2}$ were obtained from fitting the data to equation 1. CHT was used as a measure of inhibition potentials of the peptides. A one-way ANOVA in combination with Tukey post hoc test at p<0.05 level was used to probe statistical significance. Applicants' studied the effects of experimental parameters including volume, shaking and temperature on crystallization in designing a high-throughput screening assay. Applicants have shown the logistic model effectively represents the three phases: induction, crystal growth and equilibrium observed in our setup, and CHT ($t_{1/2}$) can be used as a measure of efficacy of potential crystal growth modifiers. The peptide library screened comprised of Asp and Ala residues (peptides D1-D13) at optimized assay conditions of 37° C., crystallization volume of 600 μL in a shaking environment. The lead candidates D1, D9 and D13 identified by the high-throughput assay in this study agree with the potent inhibitors from ion selective electrode (ISE) studies. A single time point measurement at 6 hour was shown to be of effective use to evaluate the inhibition potential of modifiers, and thus increase the throughput of the assay. The high throughput of the assay provides the opportunity to assess the growth modulation potential of crystal growth modifiers at varying modifier concentrations, supersaturations and ionic strengths with relative ease. The lead candidates identified from the screening can be characterized in depth for studying the effect of modifiers on crystal morphology using microscopy techniques and using molecular simulation studies to understand the modifier—crystal interactions. Finally, the assay can be translated to other crystallization systems in a relatively straightforward fashion for rational design and discovery of growth modifiers for specific applications.

TABLE 1

Crystallization half-time (CHT), standard error (SE), and residual fit of the model in equation 1 to the results of the high-throughput colorimetric calcium depletion assay for peptides D1-D13.

| Peptide | Sequence | CHT (hr) | SE in CHT | $R^2$ |
|---|---|---|---|---|
| D1 | DDDAAAADDDAAAAADD | 6.482 | 0.868 | 0.924 |
| D2 | AADAAAAADDAAAADAAA | 3.533 | 2.005 | 0.91 |

TABLE 1-continued

Crystallization half-time (CHT), standard error (SE), and residual fit of the model in equation 1 to the results of the high-throughput colorimetric calcium depletion assay for peptides D1-D13.

| Peptide | Sequence | CHT (hr) | SE in CHT | $R^3$ |
|---|---|---|---|---|
| D3 | ADAAADAADAADDAADAA | 4.142 | 0.468 | 0.953 |
| D4 | ADAADAADAADAADAADA | 4.432 | 0.749 | 0.903 |
| D5 | ADAADDAADAADDAAAAA | 4.641 | 0.361 | 0.972 |
| D6 | ADAAADDDAAADAAADDD | 5.041 | 0.568 | 0.947 |
| D7 | ADAAADDAAAAAAADAA | 5.771 | 0.474 | 0.971 |
| D8 | ADAAADDAAADAAAADAA | 4.792 | 1.29 | 0.791 |
| D9 | ADAAADDAAADAAADDAA | 7.277 | 0.365 | 0.983 |
| D10 | ADAADAAADAADDAADAA | 6.054 | 0.651 | 0.951 |
| D11 | ADAADDAAAAADAADAA | 5.767 | 1.231 | 0.859 |
| D12 | ADDAADAADAADDAADDA | 7.135 | 0.321 | 0.989 |
| D13 | ADADADADADADADADAD | 8.114 | 0.659 | 0.964 |
| Control | | 4.18 | 0.783 | 0.926 |

EXAMPLE 9

Comparison of Glu and Asp Peptide Libraries on COM Crystallization

A comparison between five Asp-Ala peptides and five Glu-Ala peptides with comparable sequences on COM crystal morphology is shown in FIG. 1. Preliminary results indicate that the Glu-Ala peptides and Asp-Ala peptides have nearly identical effects on COM crystal habit.

A quantitative comparison of peptide efficacy for inhibiting COM crystallization was performed using in situ ISE measurements. The percent inhibition in COM growth rate was calculated using the relative difference in ISE slopes in the presence of 20 μg/mL peptide. The ISE results reveal that there is a nontrivial relationship between peptide efficacy and its sequence. The effect of Asp with Glu in peptide sequences was measured on COM growth inhibition (Table 2). Results from these studies show that peptides with identical sequences (but different acidic amino acid groups) have different effects on COM growth. For instance, there is a notable difference between the effect of Asp-Ala peptides and Glu-Ala peptides on COM growth inhibition. Among the three peptide sequences compared in Table 2, the glutamic acid substation (X=E) is more effective than the aspartic acid groups (X=D).

TABLE 2

Comparison of Glu-Ala and Asp-Ala peptides efficacy

| | % inhibition | |
|---|---|---|
| Sequence | X = D | X = E |
| AXAAXAAXAAXAAXAAXA | 21 ± 10 | 40 ± 18 |
| AXAAAXXAAAXAAAXXAA | 36 ± 8 | 36 ± 21 |
| AXAAXAAAXAAXXAAXAA | 36 ± 5 | 52 ± 16 |

REFERENCES

1. George, A. and A. Veis, *Phosphorylated Proteins and Control over Apatite Nucleation, Crystal Growth, and Inhibition*. Chemical Reviews, 2008. 108(11): p. 4670-4693.
2. Weiner, S. and L. Addadi, *Crystallization Pathways in Biomineralization*, in Annual Review of Materials Research, Vol 41, D. R. Clarke and P. Fratzl, Editors. 2011. p. 21-40.
3. Stamatelou, K. K., M. E. Francis, C. A. Jones, L. M. Nyberg, and G. C. Curhan, *Time trends in reported prevalence of kidney stones in the United States: 1976-1994*. Kidney International, 2003. 63(5): p. 1817-1823.
4. Brikowski, T. H., Y. Lotan, and M. S. Pearle, *Climate-related increase in the prevalence of urolithiasis in the United States*. Proc Natl Acad Sci USA, 2008. 105(28): p. 9841-6.
5. Coe, F. L., J. H. Parks, and J. R. Asplin, *Medical process—the pathogenesis and treatment of kidney-stones*. New England Journal of Medicine, 1992. 327(16): p. 1141-1152.
6. Sizemore, J. P. and M. F. Doherty, *A New Model for the Effect of Molecular Imposters on the Shape of Faceted Molecular Crystals*. Crystal Growth & Design, 2009. 9(6): p. 2637-2645.
7. Weissbuch, I., L. Addadi, M. Lahav, and L. Leiserowitz, *Molecular Recognition at Crystal Interfaces*. Science, 1991. 253(5020): p. 637-645.
8. Asplin, J. R., D. Arsenault, J. H. Parks, F. L. Coe, and J. R. Hoyer, *Contribution of human uropontin to inhibition of calcium oxalate crystallization*. Kidney International, 1998. 53(1): p. 194-199.
9. De Yoreo, J. J., S. R. Qiu, and J. R. Hoyer, *Molecular modulation of calcium oxalate crystallization*. American Journal of Physiology-Renal Physiology, 2006. 291(6): p. F1123-F1131.
10. Guo, S. W., M. D. Ward, and J. A. Wesson, *Direct visualization of calcium oxalate monohydrate crystallization and dissolution with atomic force microscopy and the role of polymeric additives*. Langmuir, 2002. 18(11): p. 4284-4291.
11. Wang, L. J., W. Zhang, S. R. Qiu, W. J. Zachowicz, X. Y. Guan, R. K. Tang, J. R. Hoyer, J. J. De Yoreo, and G. H. Nancollas, *Inhibition of calcium oxalate monohydrate crystallization by the combination of citrate and osteopontin*. Journal of Crystal Growth, 2006. 291(1): p. 160-165.
12. Jung, T., X. X. Sheng, C. K. Choi, W. S. Kim, J. A. Wesson, and M. D. Ward, *Probing crystallization of calcium oxalate monohydrate and the role of macromolecule additives with in situ atomic force microscopy*. Langmuir, 2004. 20(20): p. 8587-8596.
13. Wesson, J. A., E. M. Worcester, and J. G. Kleinman, *Role of anionic proteins in kidney stone formation: Interaction between model anionic polypeptides and calcium oxalate crystals*. Journal of Urology, 2000. 163(4): p. 1343-1348.
14. Taller, A., B. Grohe, K. A. Rogers, H. A. Goldberg, and G. K. Hunter, *Specific adsorption of osteopontin and synthetic polypeptides to calcium oxalate monohydrate crystals*. Biophysical Journal, 2007. 93(5): p. 1768-1777.
15. Friddle, R. W., M. L. Weaver, S. R. Qiu, A. Wierzbicki, W. H. Casey, and J. J. De Yoreo, *Subnanometer atomic force microscopy of peptide-mineral interactions links clustering and competition to acceleration and catastrophe*. Proceedings of the National Academy of Sciences of the United States of America, 2010. 107(1): p. 11-15.
16. Grohe, B., B. P. H. Chan, E. S. Sorensen, G. Lajoie, H. A. Goldberg, and G. K. Hunter, *Cooperation of phos-* phates and carboxylates controls calcium oxalate crystallization in ultrafiltered urine. Urological Research, 2011. 39(5): p. 327-338.
17. Grohe, B., J. O'Young, D. A. Ionescu, G. Lajoie, K. A. Rogers, M. Karttunen, H. A. Goldberg, and G. K. Hunter, Control of calcium oxalate crystal growth by face-specific adsorption of an osteopontin phosphopeptide. Journal of the American Chemical Society, 2007. 129(48): p. 14946-14951.
18. Wang, L. J., X. Y. Guan, R. K. Tang, J. R. Hoyer, A. Wierzbicki, J. J. De Yoreo, and G. H. Nancollas, Phosphorylation of osteopontin is required for inhibition of calcium oxalate crystallization. Journal of Physical Chemistry B, 2008. 112(30): p. 9151-9157.
19. Weaver, M. L., S. R. Qiu, R. W. Friddle, W. H. Casey, and J. J. De Yoreo, How the Overlapping Time Scales for Peptide Binding and Terrace Exposure Lead to Nonlinear Step Dynamics during Growth of Calcium Oxalate Monohydrate. Crystal Growth & Design, 2010. 10(7): p. 2954-2959.
20. DeOliveira, D. B. and R. A. Laursen, Control of calcite crystal morphology by a peptide designed to bind to a specific surface. Journal of the American Chemical Society, 1997. 119(44): p. 10627-10631.
21. Long, J. R., J. L. Dindot, H. Zebroski, S. Kiihne, R. H. Clark, A. A. Campbell, P. S. Stayton, and G. P. Drobny, A peptide that inhibits hydroxyapatite growth is in an extended conformation on the crystal surface. Proceedings of the National Academy of Sciences of the United States of America, 1998. 95(21): p. 12083-12087.
22. Kim, I. W., S. Collino, D. E. Morse, and J. S. Evans, A crystal modulating protein from molluscan nacre that limits the growth of calcite in vitro. Crystal Growth & Design, 2006. 6(5): p. 1078-1082.
23. Silverman, L. D., M. Saadia, J. S. Ishal, N. Tishbi, E. Leiderman, I. Kuyunov, B. Recca, C. Reitblat, and R. Viswanathan, Hydroxyapatite Growth Inhibition by Osteopontin Hexapeptide Sequences. Langmuir, 2010. 26(12): p. 9899-9904.
24. Elhadj, S., E. A. Salter, A. Wierzbicki, J. J. De Yoreo, N. Han, and P. M. Dove, Peptide controls on calcite mineralization: Polyaspartate chain length affects growth kinetics and acts as a stereochemical switch on morphology. Crystal Growth & Design, 2006. 6(1): p. 197-201.
25. Shiba, K. and T Minamisawa, A synthesis approach to understanding repeated peptides conserved in mineralization proteins. Biomacromolecules, 2007. 8(9): p. 2659-2664.
26. Sheng, X. X., T. S. Jung, J. A. Wesson, and M. D. Ward, Adhesion at calcium oxalate crystal surfaces and the effect of urinary constituents. Proceedings of the National Academy of Sciences of the United States of America, 2005. 102(2): p. 267-272.
27. Graether, S. P., M. J. Kuiper, S. M. Gagne, V. K. Walker, Z. C. Jia, B. D. Sykes, and P. L. Davies, beta-helix structure and ice-binding properties of a hyperactive antifreeze protein from an insect. Nature, 2000. 406 (6793): p. 325-328.
28. Doxey, A. C., M. W. Yaish, M. Griffith, and B. J. McConkey, Ordered surface carbons distinguish antifreeze proteins and their ice-binding regions. Nature Biotechnology, 2006. 24(7): p. 852-855.
29. Qiu, S. R. and C. A. Orme, Dynamics of Biomineral Formation at the Near-Molecular Level. Chemical Reviews, 2008. 108(11): p. 4784-4822.
30. Gray, J. J., The interaction of proteins with solid surfaces. Current Opinion in Structural Biology, 2004. 14(1): p. 110-115.
31. Wang, L. J., S. R. Qiu, W. Zachowicz, X. Y. Guan, J. J. DeYoreo, G. H. Nancollas, and J. R. Hoyer, Modulation of calcium oxalate crystallization by linear aspartic acid-rich peptides. Langmuir, 2006. 22(17): p. 7279-7285.
32. Azzopardi, P. V., J. O'Young, G. Lajoie, M. Karttunen, H. A. Goldberg, and G. K. Hunter, Roles of Electrostatics and Conformation in Protein-Crystal Interactions. Plos One, 2010. 5(2).
33. Qiu, S. R., A. Wierzbicki, C. A. Orme, A. M. Cody, J. R. Hoyer, G. H. Nancollas, S. Zepeda, and J. J. De Yoreo, Molecular modulation of calcium oxalate crystallization by osteopontin and citrate. Proceedings of the National Academy of Sciences of the United States of America, 2004. 101(7): p. 1811-1815.
34. Coe, F. L. and J. R. Asplin, Stopping the Stones. Science, 2010. 330(6002): p. 325-326.

What is claimed is:

1. A composition for inhibiting calcium oxalate monohydrate crystal growth comprising:
   at least one isolated polypeptide, and
   at least one pharmaceutically acceptable carrier;
   wherein the isolated polypeptide comprises an amino acid sequence selected from the group consisting of DDDAAAAADDDAAAAADD (SEQ ID NO: 1), AADAAAAADDAAAADAAA (SEQ ID NO: 2), ADAAADAADAADDAADAA (SEQ ID NO: 3), ADAADDAADAADDAAAAA (SEQ ID NO: 5), ADAAADDDAAADAAADDD (SEQ ID NO: 6), ADAAADDAAAAAAADAA (SEQ ID NO: 7), ADAAADDAAADAAAADAA (SEQ ID NO: 8), ADAAADDAAADAAADDAA (SEQ ID NO: 9), ADAADAAADAADDAADAA (SEQ ID NO: 10), ADAADDAAAAAADAADAA (SEQ ID NO: 11), ADDAADAADAADDAADDA (SEQ ID NO: 12), AAEAAAAAEEAAAAEAAA (SEQ ID NO: 14), AEAAAEAAEAAEEAAEAA (SEQ ID NO: 15), AEAAAEEAAAEAAAAEAA (SEQ ID NO: 17), AEAAAEEAAAEAAAEEAA (SEQ ID NO: 18), AEAAEAAAEAAEEAAEAA (SEQ ID NO: 19), AEAAEEAAAAAAEAAEAA (SEQ ID NO: 20), AEEAAEAAEAAEEAAEEA (SEQ ID NO: 21), and AEEAEEAEEAEEAEEAEE (SEQ ID NO: 22), or consists of an amino acid sequence selected from the group consisting of ADAADAADAADAADAADA (SEQ ID NO: 4), ADADADADADADADADAD (SEQ ID NO: 13), AEAAEAAEAAEAAEAAEA (SEQ ID NO: 16), AEAEAEAEAEAEAEAEAE (SEQ ID NO: 23), and EEEEEEEEEEEEEEEEEE (SEQ ID NO: 24); and wherein the isolated polypeptide inhibits calcium oxalate monohydrate crystal growth.

2. A method of controlling calcium oxalate monohydrate crystal growth in a subject in need thereof comprising administering to the subject a therapeutically effective amount of the composition of claim 1.

3. The method of claim 2, wherein the subject has kidney stone disorder.

4. The method of claim 2, wherein the subject has renal calcification disorder.

5. The method of claim 2, further comprising using ultrasound therapy.

* * * * *